US005753787A

United States Patent [19]
Hawdon et al.

[11] Patent Number: 5,753,787
[45] Date of Patent: May 19, 1998

[54] NUCLEIC ACIDS ENCODING ANCYLOSTOMA SECRETED PROTEIN

[75] Inventors: John M. Hawdon, Westbrook; Peter J. Hotez, Cheshire; Brian F. Jones, Shelton, all of Conn.

[73] Assignee: Yale University, New Haven, Conn.

[21] Appl. No.: 419,414

[22] Filed: Apr. 10, 1995

[51] Int. Cl.$^6$ .................... C07H 19/00; C07H 21/02; C12N 15/09; C12P 19/36
[52] U.S. Cl. ............... 536/22.1; 536/23.1; 536/23.7; 536/24.3; 435/90; 435/91.1; 435/252.3; 435/320.1
[58] Field of Search ................... 435/69.1, 69.3, 435/71.1, 320.1, 252.1, 71.3; 536/22.1, 23.7

[56] References Cited

U.S. PATENT DOCUMENTS

| | | | |
|---|---|---|---|
| 4,563,417 | 1/1986 | Albarella et al. | 435/6 |
| 4,581,333 | 4/1986 | Kourilsky et al. | 435/6 |
| 4,683,195 | 7/1987 | Mullis et al. | 435/6 |
| 4,683,202 | 7/1987 | Mullis | 435/6 |
| 4,732,847 | 3/1988 | Stuart et al. | 435/6 |
| 4,743,535 | 5/1988 | Carrico | 435/6 |
| 4,786,600 | 11/1988 | Kramer et al. | 435/6 |
| 4,833,084 | 5/1989 | Carrico et al. | 435/6 |
| 4,851,331 | 7/1989 | Vary et al. | 435/6 |
| 4,882,269 | 11/1989 | Schneider et al. | 435/6 |
| 4,957,858 | 9/1990 | Chu et al. | 435/6 |
| 4,965,188 | 10/1990 | Mullis et al. | 435/6 |
| 4,994,373 | 2/1991 | Stavrianopoulos et al. | 435/6 |

FOREIGN PATENT DOCUMENTS

| | | | |
|---|---|---|---|
| 2-131599 | 5/1990 | Japan | C12Q 1/68 |
| WO87/03622 | 6/1987 | WIPO | C12Q 1/68 |
| WO89/06700 | 7/1989 | WIPO | C12Q 1/68 |
| WO91/10746 | 7/1991 | WIPO | C12Q 1/68 |
| WO91/17442 | 11/1991 | WIPO | G01N 33/539 |
| WO92/12261 | 7/1992 | WIPO | C12Q 1/68 |
| 9213890 | 8/1992 | WIPO | C07K 15/08 |
| WO92/14843 | 9/1992 | WIPO | C12Q 1/68 |

OTHER PUBLICATIONS

Hotez et al Infectious Agents & Disease vol. 4 pp. 71–75, 1995.
Hotez et al Scientific American Jun. 1995, pp. 42–48, vol. 272.
Hotez et al J. Biol Chemistry 260: 734 3–8, 1985.
Suggs et al PNAS 78: 6613–6617, 1981.
Houghten Vaccine 86 pp. 21–25.
Hotez et al Scientific American 272: 68–74, 1995 Hookworm Infection.
Hotez Peter Jay Dissertation Abstr. Int B 1987 47(10) p. 4145 Identification, Isolation, and Molecular Cloning of a Hookworm Protease, an Approach Towards a Defined Vaccine for Ancylosotomiasis.
Allison and Byars, "An adjuvant formulation that selectively elicits the formation of antibodies of protective isotypes and of cell–mediated immunity." *J. Immunol. Methods* 95:157 (1986).

Arheim, N. and Erlich, H., "Polymerase chain reaction strategy." *Annual Review of Biochemistry* 61:131–156 (1992).
Bektesh and Hirsh, "*C elegans* mRNA's acquire a spliced leader through a trans–splicing mechanism." *Nucleic Acids Research* 16:5692 (1988).
Bitter, et al., "Expression and Secretion Vectors for Yeast," *Methods in Enzymology* 153:516–544 (Wu and Grossman, eds., Academic Press, 1987).
Boguslawski, et al., "Characterization of monoclonal antibody to DNA–RNA and its application to immunodetection of hybrids." *J. Immunol. Methods* 89:123–130 (1986).
Byars and Allison, "Adjuvant formulation for use in vaccines to elicit both cell–mediated and humoral immunity." *Vaccine* 5:223 (1987).
Cappello, et al., "Ancylostoma Factor Xa Inhibitor: Partial Purification and Its Identification as a Major Hookworm–Derived Anticoagulant In Vitro." *J. Infec. Dis.* 167:1474–7 (1993).
Cappello, et al., "*Ancylostoma caninum* anticoagulant peptide: A hookworm–derived inhibitor of human coagulation factor xa." *Proc. Natl. Acad. Sci. USA* 92:6152–6156 (1995).
Chu, et al., "Syntheisis of an amplifiable reporter RNA for bioassays," *Nucl. Acids Res.* 14:5591–5603 (1986).
Cook, "Use of Benzimidazole Chemotherapy in Huamn Helminthiases: Indications and Efficacy." *Parasitol. Today* 6:133–136 (1990).
Cullen, et al., "Molecular Cloning Vectors for Aspergillus and Neurospora," *A Survey of Molecular Cloning Vectors and their Uses* Chapter 21:419–433 (Butterworth Publishers, Stoneham, MA 1986).
Cullen, et al., "Controlled Expression and Secretion of Bovine Chymosin in *Aspergillus nidulans*." *Bio/Technology* 5:369–378 (1987).
Dayhoff, et al., "Establishing Homologies in Protein Sequences," *Methods in Enzymology* 91:524–545 (1983).
Donnelly, et al., "Immunization with DNA." *J. Immunol. Methods* 176(2):145–152 (1994).

(List continued on next page.)

Primary Examiner—Hazel F. Sidberry
Attorney, Agent, or Firm—Arnall Golden & Gregory, LLP

[57] ABSTRACT

A protein, Ancylostoma Secreted Protein (ASP), that is released by hookworm larvae following infection, and which is highly immunogenic in experimental animals, is disclosed. Nucleic acids encoding ASP, antibodies recognizing ASP, and methods of detecting ASP, nucleic acids encoding ASP, and antibodies recognizing ASP, in a sample are also disclosed. ASP is useful in a vaccine for hookworm as well as other soil–transmitted human and veterinary nematodiases. ASP is also useful as a target for specific treatment of hookworm, and can be used in a diagnostic assay for hookworm, using standard protein detection techniques, especially those based on antibodies. DNA encoding ASP is useful both for producing ASP recombinantly and in a diagnostic assay for hookworm. Antibodies recognizing ASP are useful in diagnostic assays to detect protein produced during hookworm infection.

4 Claims, No Drawings

OTHER PUBLICATIONS

Duffaud, et al., "Expression and Secretion of Foreign Proteins in *Escherichia coli,*" *Methods in Enzymology* 153:492–506 (Wu and Grossman, eds., Academic Press, 1987).

Eisinstein, "Phase Variation of Type 1 Fimbriae in *Escherichia coli* Is Under Transcriptional Control," *Science* 214:337–338 (1981).

Eldridge, et al., "Biodegradable Microspheres: Vaccine Delivery System for Oral Immunization," *Current Topics in Microbiology and Immunology* 146:59–66 (1989).

Frohman, M.A., et al., "Rapid production of full-length cDNA from rate transcripts: amplification using a single gene-specific oligonucleotide primer," *Proc. Natl. Acad. Sci. USA* 85: 8998–9002 (1988).

Galfré and Milstein, "Preparation of Monoclonal Antibodies: Strategies and Procedures," *Methods Enzymol.* 73:3–46 (1981).

Gilles, H. M., "Selective primary health care: strategies for control of disease in the developing world. XVII. Hookworm infection and anemia," *Reviews of Infectious Diseases* 7:111–118 (1985).

Gilles, H., Naturally acquired infections: what's needed? In "Hookworm Disease: Current Status and New Directions" (G. A. Schad and K. S. Warren, Eds.), pp. 221–230. Taylor and Francis, London (1990).

Goodman-Snitkoff, et al., "Role of Intrastructural/Intermolecular Help in Immunization with Peptide-Phospholipid Complexes.," *J. Immunol.* 147:410–415 (1991).

Gray, et al., "Primary structure of *Mucor miehei* aspartyl protease: evidence for a zymogen intermediate," *Gene* 48:41–53 (1987).

Grunstein, et al., "colony hybridization: A method for the isolation of cloned DNAs that contain a specific gene," *Proc. Natl. Acad. Sci. USA* 72:3961 (1975).

Guarelli, et al., "Isothermal, in vitro, amplication of nucleic acids by a multienzyme reaction modeled after retroviral replication," *Proc. Natl. Acad. Sci. USA* 87:1874–1878 (1990).

Hainan, et al., "Effect of Albendazole on the Larvae and Eggs of *Necator Americanus* in Golden Hamster," *Chinese Journal of Parasitology & Parasitic Diseases* 12:200–204 (1994).

Harada, et al., "Monoclonal antibody G6K12 specific for membrane-associated differentiation marker of human stratified squamous epithelia and squamous cell carcinoma," *J. Oral Pathol. Med.* (Denmark) 22(4):145–152 (Apr. 1993).

Hattori and Sakald, "Dideoxy sequencing method using denatured plasmid templates," *Analytical Biochemistry* 152:232–238 (1988).

Hawdon, et al., "Cloning and Characterization of Ancylostoma Secreted Protein: a Novel Protein Associated with the Transition to Parasitism by Infective Hookworm Larvae," *J. Biol. Chem.* (In Press, 1996).

Hawdon and Schad, "Serum-Stimulated Feeding in Vitro by Third-Stage Infective Larvae of the Canine Hookworm *Ancylostoma caninum,*" *J. Parasitol.* 76:394–398 (1990).

Hawdon and Schad, "Albumin and a Dialyzable Serum Factor Stimulate Feeding in Vitro by Third-Stage Larvae of the Canine Hookworm *Ancylostoma caninum,*" *J. Parasitol.* 77:587–591 (1991).

Hawdon and Schad, "*Ancylostoma caninum*: Glutathione Stimulates Feeding in Third-Stage Larvae by a Sulfhydryl-Independent Mechanism," *Experimental Parasitology* 77:489–491 (1993).

Hawdon, et al., "*Ancylostoma caninum*: Metalloprotease Release Coincides with Activation of Infective Larvae in Vitro," *Experimental* Parasitology 80:205–211 (1995).

Hawdon and Schad, "Long-term storage of hookworm infective larvae in buffered saline solution maintains larval responsiveness to host signals," *Journal of the Helminthological Society of Washington* 58:140–142 (1991).

Hotez, P. J., "Hookworm disease in children," *Pediatric Infectious Disease Journal* 8:516–520 (1989).

Hotez and Pritchard, "Hookworm Infection," *Sci. Amer.* 272:42–48 (1995).

Hotez, et al., "Hookworm Larval Infectivity, Arrest and Amphiparatenesis: The *Caenorhabditis elegans* Daf–c Paradigm," *Parasitol. Today* 9:23–26 (1993).

Hotez, et al., "Hookworm Antigens: the Potential for Vaccination," *Parasitol. Today* 3:247–249 (1987).

Hotez, et al., "Metalloproteases of Infective Ancylostoma Hookworm Larvae and Their Possible Functions in Tissue Invasion and Ecdysis," *Infect. Immun.* 58:3883–3894 (1990).

Hotez, et al., "Molecular Pathobiology of Hookworm Infection," *Infect. Agents and Disease* 4:71–75 (1995).

Inai, et al., "Immunohistochemical detection of an enamel protein-related epitope in rat bone at an early stage of osteogenesis," *Histochemistry* (Germany) 99(5):335–362 (May 1993).

Jain and Gomer, "Increasing specificity from the PCR-RACE technique," *Biotechniques* 12:58–59 (1992).

Johnstone and Thorpe, *Immunochemistry in Practice,* Second edition (Blackwell Scientific Publication, Oxford, 1987).

Kalkofen, "Hookworms of Dogs and Cats," *Veterinary Clinics of North America: Small Animal Practice* 17:1341–1354 (1987).

Kirkpatrick, "Epizootiology of endoparasitic infections in pet dogs and cats presented to a veterinary teaching hospital," *Veterinary Parasitology* 30:113–124 (1988).

Koren, et al., "Characterization of a monoclonal antibody that binds equally to all apolipoprotein and lipoprotein forms of human plasma apolipoprotein B. I. Specificity and binding studies," *Biochim. Biophys. Acta* 876:91–100 (1986).

Kreuter, *Microcapsules and Nanoparticles in Medicine and Pharmacology,* pp. 125–148 (M. Donbrow, ed., CRC Press, 1991).

Kwoh, et al., "Transcription-based amplification system and detection of amplified human immunodeficiency virus type 1 with a bead-based sandwich hybridization format," *Proc. Natl. Acad. Sci. USA* 86:1173–1177 (1989).

Laemmli, "Cleavage of structural proteins during the assembly of the head of bacteriophage T4," *Nature (London)* 227, 680–685 (1970).

Lewis and Dean, "Automated site-directed drug design: the concept of spacer skeletons for primary structure generation," *Proc. R. Soc. Lond.* 236:125–140 (1989).

Lewis and Dean, "Automated site-directed drug design: the formation of molecular templates in primary structure generation," *Proc. R. Soc. Lond.* 236:141–162 (1989).

Lillis, "Helminth Survey of Dogs and Cats in New Jersey," *Journal of Parasitology* 53:1082–1084 (1967).

Lin and Tang, "Synthesis, Purification, and Active Site Mutagenesis of Recombinant Porcine Pepsinogen," *J. Biol. Chem.* 264:4482–4489 (1989).

Liu, Shu–xian, et al., "The Antigenicity of GST Antigen Extracted from Chinese Strain of *Schistosoma japonicum*," *SE Asian J. Trop. Med. Pub. Health* 24:61–65 (1993).

Liu, "Medical Progress in China: An Overview of Molecular Parasitology in China," *Chin. Med. J.* 105:91–96 (1992).

Liu, et al., *SE Asian J. Trop. Med. Pub. Health* 24:61–64 (1993)*.

Liu, et al., "Comparative Study on Antigenicity and Immunogenicity of 26–28 kDa Antigen and Recombinant SJ26 (RSJ26) of *Schistosoma japonicum*," *SE Asian J. Trop. Med. Pub. Health* 24:65–69 (1993).

Liu, et al., "The Posibility of GST Antigen from Chinese Strain of *Schistosoma japonicum* for Immunodiagnosis of Schistosomiasis," *SE Asian J. Trop. Med. Pub. Health* 24:70–73 (1993).

Liu, et al., "DNA Vaccination Induces Long–Lived $T_H1$–Like Immune Responses to HIV–1 GP120," *AIDS Research and Human Retroviruses* 10:S34 (1994).

Lowell, "Proteosomes, Hydrophobic Anchors, Iscoms, and Liposomes for Improved Presentation of Peptide and Protein Vaccines," *New Generation Vaccines* (Woodrow and Levine, eds., Marcel Dekker, NY, 1990), Ch. 12, pp. 141–160.

Lowell, et al., "Proteosome–Lipopeptide Vacines: Enhancement of Immunogenicity for Malaria CS Peptides," *Science* 240:800 (1988).

Lozoff, et al., "Long–term developmental outcome of infants with iron deficiency," *New England Journal of Medicine* 235:687–694 (1991).

Luckow and Summers, "Trends in the Development of Baculovirus Expression Vectors," *Bio/Technology* 6:47–55 (1988).

McKinaly and Rossmann, "Rational Design of Antiviral Agents," *Annu. Rev. Pharmacol. Toxiciol.* 29:111–122 (1989).

Miller, "Vaccination against canine hookworm disease," *Advances in Parasitology* 9:153–183 (1971).

Miller, et al., "Industrial Development and Field Use of the Canine Hookworm Vaccine," *Adv. Parasitol.* 16:333–342 (1978).

Mulder, et al., "Characterization of Two Human Monoclonal Antibodies Reactive with HLA–B12 and HLA–B60, Respectively, Raised by in vitro Secondary Immunization of Peripheral Blood Lymphocytes," *Hum. Immunol.* 36(3):186–192 (Mar. 1993).

Nilsen, "Trans–splicing of nematode messenger RNA," *Annual Review of Microbiology* 47:413–440 (1993).

Orr, et al., "Immunogenicity and Efficacy of Oral or Intranasal *Shigella flexneri* 2a and *Shigella sonnei* Proteosome–Lipopolysaccharide Vaccines in Animal Models," *Infect. Immun.* 61: 2390 (1993).

Perry and Davies, "The Use of 3D Modelling Databases for Identifying Structure Activity Relationships," *QSAR: Quantitative Structure–Activity Relationships in Drug Design* pp. 189–193 (Alan R. Liss, Inc. 1989).

Poorman, et al., "Isolation and Characterization of Native Human Renin Derived From Chinese Hamster Ovary Cells," *Proteins* 1:139–145 (1986).

Ren, et al., *Chin. J. Parasitol. Paras. Dis.* 12:200–204 (1994).

Ripka, "Computers picture the perfect drug," *New Scientist* 54–57 (Jun. 16, 1988).

Rotivinen, et al., 1988 *Acta Pharmaceutica Fennica* 97, 159–166*.

Rusia, et al., "Placental morphology & histochemistry in iron deficiency anaemia," *Indian J. Med. Res.* 87:468 (1988).

Sambrook, J., Fritsch, E. F. and Maniatis, T. 1989. "Molecular Cloning: A Laboratory Manual" Cold Spring Harbor, Cold Spring Harbor Laboratory Press.

Sanger, et al., "DNA sequencing with chain–terminating inhibitors," *Proceedings of the National Academy of Science USA* 74:5463–5467 (1977).

Scahill, et al., "Expression and characterization of the product of a human immune interferon cDNA gene in Chinese hamster ovary cells," *Proc. Natl. Acad. Sci., U.S.A.* 80:4654–4658 (1983).

Schad, "Arrested Development of *Ancylostoma caninum* In Dogs: Influence of Photoperiod and Temperature on Induction of a Potential to Arrest," *Aspects of Parasitology: A Festschrift Dedicated to the Fiftieth Anniversary of the Institute of Parasitology of McGill University* (Meerovitch, ed., McGill University, Montreal, pp. 361–391) (1982).

Schad and Anderson, "Predisposition to Hookworm Infection in Humans," *Science* 228:1537–1540 (1985).

Scrimshaw, "Iron Deficiency," *Scien. Amer.* 265:46–52 (1991).

Sen–hai, "Nationwide Survey of Human Parasites in China," *SE Asian J. Trop. Med. Pub. Health* 25:4–10 (1994).

Short and Sorge, "In vivo excision properties of bacteriophage lambda ZAP expression vectors," *Methods in Enzymology* 216:495–508 (1992).

Southern, "Detection of Specific Sequences Among DNA Fragments Separated by Gel Electrophoresis," *J. Mol. Biol.* 98:503 (1975).

Spieth, et al., "Operons in *C elegans*: polycistronic MRNA precursors are processed by trans–splicing of SL2 to downstream coding regions," *Cell* 73:521–532 (1993).

Stauber, et al., "Rapid generation of monoclonal antibody–secreting hybridomas against African horse sickness virus by in vitro immunization and the fusion/cloning technique," *J. Immunol. Methods* (Netherlands) 161(2):157–168 (May 26, 1993).

Stuart, et al., "Location of the 18/28S ribosomal RNA genes in two Hawaiian Drosphila species by monoclonal immunological identification of RNA–DNA hybrids in situ," *Proc. Natl. Acad. Sci., USA* 78:3751 (1981).

Sung, et al., "Short Homopeptide Leader Sequences Enhanced Production of Human Proinsulin in *Excherichia coli*," *Methods in Enzymology*, vol. 153, Chapters 23 to 34 (Wu and Grossman, eds., Academic Press, 1987).

Templeton, N. S., et al., "Reducing artifact and increasing the yield of specific DNA target fragments during PCR–RACE or anchor PCR," *Biotechniques* 15:48–51 (1993).

Venkateswaran, et al., "Production of Anti–Fibroblast Growth Factor Receptor Monoclonal Antibodies by In Vitro Immunization," *Hybridoma* 11(6):729–739 (Dec. 1992).

von Heijne, "A new method for predicting signal sequences cleavage sites," *Nucleic Acids Research* 14:4683–4690 (1986).

Willadsen, "Immunological Approaches to the control of Ticks," *Int. J. Parasitol.* 17:671 (1987).

Xiao, et al., *Chin. J. Parasitol. Paras. Dis.* 12:214–17 (1994).

Yu, et al., *Chin. J. Parasitol. Paras. Dis.* 12:241–248 (1994)*.

The 1995 Lab Manual Source Book (Cold Spring Harbor Laboratory Press, NY, 1995).

NUCLEIC ACIDS ENCODING ANCYLOSTOMA SECRETED PROTEIN

This invention was made with government support under Grant Numbers R29-AI32726 awarded by the Department of Health and Human Services. The government has certain rights in the invention.

BACKGROUND OF THE INVENTION

The present invention is generally in the area of treatments and diagnostics for hookworm infection.

Hookworm disease continues to rank among the most important infectious diseases on a world-wide basis. Over 20% of the world population is infected, and hookworms are the leading cause of anemia in the tropics (Gilles, *Reviews of Infectious Diseases* 7: 111–118 (1985)). In China alone, an estimated 194 million people are infected with hookworm, with up to 50 percent prevalence in the agriculturally rich areas along the Yangtze River.

Adult hookworms attach to the mucosa of the small intestine and feed on blood, resulting in the loss of up to 0.26 mL of blood per worm per day (Gilles, *Hookworm Disease: Current Status and New Directions* (Schad and Warren, Eds., Taylor and Francis, London, 1990), pages 221–230). The subsequent iron deficiency anemia is especially devastating to children, resulting in stunted physical and cognitive development, which may be permanent (Lozoff et al., *New England Journal of Medicine* 235: 687–694 (1991)). Furthermore, acute neonatal hookworm disease, resulting from the lactogenic transmission of infective stages to nursing children, is often fatal (Hotez, *Pediatric Infectious Disease Journal* 8: 516–520 (1989)).

Despite the availability of effective chemotherapeutic agents, hookworm remains a serious geohelminth infection. This is due to several factors. First, many of the latest generation of anthelminthics are prohibitively expensive, and therefore unaffordable by the developing countries that would benefit most from their use. Secondly, there is no sterile immunity developed following hookworm infection, such that people treated with anthelminthics are quickly re-infected when they are re-exposed to infective stages. Third, previously unreported toxicities have been now observed with wide scale use of anthelminthic drugs including seizures, encephalitis and deafness. Fourth, disappointing efficacy has been noted with the conventional anthleminthic drugs.

An effective and inexpensive recombinant vaccine would provide an affordable approach to controlling the ravages of hookworm disease.

There is also a need for a vaccine against canine hookworm. Prevalence estimates range from 27% of stray dogs in New Jersey (Lillis, *Journal of Parasitology* 53: 1082–1084 (1967)) to 14% of dogs presented to an urban veterinary teaching hospital (Kirkpatrick, *Veterinary Parasitology* 30: 113–124 (1988)). Neonatal ancylostomiasis caused by vertical transmission of arrested *A. caninum* third-stage larvae ($L_3$) continues to be a serious problem, often resulting in fatal exsanguination of puppies (Kalkofen, *Veterinary Clinics of North America: Small Animal Practice* 17: 1341–1354 (1987)).

Experimental evidence suggests that vaccination holds promise as an effective hookworm control strategy. Using the canine hookworm as a model system, Miller was able to prevent anemia and hookworm disease in dogs vaccinated with an attenuated larval vaccine (Miller, *Adv. Parasitol* . 9: 153–183 (1971)). Although a commercial failure for technical and logistical reasons; primarily due to short shelf life and the requirement for special handling; the vaccine demonstrated that the serious effects of hookworm disease could be reduced or eliminated by vaccination. Instead of preventing infection, the vaccine decreased the pathogenicity and fecundity of worms in the challenge infection, thereby preventing anemia in the challenged animals. Although this vaccine was effective in preventing symptoms of hookworm disease in dogs, such a vaccine would be both risky to use in humans and prohibitively expensive to produce and distribute. Moreover, it would be impossible to harvest the quantities of feces required in order to accumulate sufficient numbers of infective larvae. Therefore, the X-irradiated larval vaccine is not an option for use in humans.

However, if similar results could be obtained with a recombinant vaccine, neither risk nor cost should hamper its widespread use. To date, there has been little interest in the production of a recombinant vaccine, mostly because of an absence of promising target molecules.

It is therefore an object of the present invention to provide a method and means for vaccinating people and other animals against hookworm infection.

It is a further object of the present invention to provide a hookworm vaccine that can be prepared using recombinant genetically engineered hookworm proteins and fragments thereof.

It is another object of the present invention to provide a target for selective hookworm treatment.

It is still another object of the present invention to provide a diagnostic for hookworm infection.

SUMMARY OF THE INVENTION

A protein that is released by hookworm larvae following infection, and which is highly immunogenic in experimental animals, has been identified. The protein has been designated Ancylostoma Secreted Protein (ASP). ASP has an apparent molecular weight of 37–40 kDa. ASP from *Ancylostoma caninum* contains 406 amino acids. The pro-form of ASP contains an 18 amino acid secretion signal sequence which does not appear in mature ASP. ASP is released from larval *A. caninum* that begin feeding.

DNA encoding the protein has been isolated. The protein can be made by recombinant means in a variety of hosts. The recombinant protein, or immunogenic fragments thereof, can be formulated as a vaccine. The recombinant protein, or antibodies to the protein, can also be used in an assay to detect hookworm infection. DNA encoding all or parts of the protein can be used as probes to detect the presence of hookworm nucleic acid. Such probes are useful in assays of tissue samples, body fluid samples, and hookworm infection sources.

DETAILED DESCRIPTION OF THE INVENTION

Ancylostoma Secreted Protein

A protein that is released by hookworm larvae following infection, designated Ancylostoma Secreted Protein, is disclosed. The protein has an apparent molecular weight of 37–40 kDa. ASP from *Ancylostoma caninum* contains 406 amino acids. The pro-form of ASP contains an 18 amino acid secretion signal sequence which does not appear in mature ASP. The sequence of *A. caninum* ASP is listed as SEQ ID NO:2. This sequence includes the 18 amino acid secretion signal sequence. ASP is released from larval *A. caninum* that begin feeding. Larvae begin feeding at the transition from the free-living stage to the parasitic stage. ASP is thought to be involved in this transition.

This is demonstrated by data showing that ASP is released within 30 minutes of activation of larval feeding in vitro, and that ASP is released continuously once the $L_3$ have been activated. Inhibition of activation with 4,7-phenanthroline prevents the release of ASP. The specific, rapid release of ASP by activated infective larvae indicates that ASP has a role in the transition to parasitism, and as such is a desirable target for a recombinant vaccine against hookworm disease.

As used herein, Ancylostoma Secreted Protein and ASP refer to a protein having the amino acid sequence shown in SEQ ID NO:2 from amino acid 19 to amino acid 424; derivatives thereof with conservative amino acid substitutions, deletions, or additions; any homolog or allelic form of ASP produced in nematodes; any protein having at least 40% amino acid sequence identity with amino acids 19 to 424 of SEQ ID NO:2; or any protein that is immunoreactive with an antibody immunoreactive with the ASP of SEQ ID NO:2 but that is not immunoreactive with hymenoptera proteins. Preferred ASP derivatives have an amino acid sequence identity with amino acids 19 to 424 of SEQ ID NO:2 of greater than 40%, such as at least 50% amino acid sequence identity, at least 60% amino acid sequence identity, or at least 70% amino acid sequence identity. Preferably, ASP derivatives have at least 80% amino acid sequence identity; more preferably, at least 90% amino acid sequence identity; and most preferably, at least 95% amino acid sequence identity with amino acids 19 to 424 of SEQ ID NO:2.

As used herein, percent amino acid sequence identity is calculated as the percentage of aligned amino acids that match the reference sequence, where the sequence alignment has been determined using the alignment algorithm of Dayhoff et al., *Methods in Enzymology* 91: 524–545 (1983). Here the reference sequence is amino acids 19 to 424 of SEQ ID NO:2. Unless otherwise stated, all amino acid position references use the numbering shown in SEQ ID NO:2. As used herein, immunoreactivity is determined by any standard technique for detecting antibody-antigen interactions. Many assays useful for determining immunoreactivity are described in Johnstone and Thorpe, *Immunochemistry in Practice*, Second edition (Blackwell Scientific Publications, Oxford, 1987). Preferred assays are the immunoassays described on pages 241 to 260 of Johnstone and Thorpe.

In the case of immunogenic fragments of ASP, preferred fragments are those that are not immunoreactive with antibodies that are immunoreactive to proteins other than ASP. Accordingly, preferred immunogenic fragments of ASP have an amino acid sequence with at least five consecutive amino acids that are present in an ASP as defined above, where no amino acid sequence of five or more, six or more, seven or more, or eight or more consecutive amino acids present in the immunogenic fragment of ASP is present in a protein other than ASP. More preferred immunogenic fragments of ASP have an amino acid sequence of at least five consecutive amino acids in SEQ ID NO:2, where no amino acid sequence of five or more, six or more, seven or more, or eight or more, consecutive amino acids present in the immunogenic fragment of ASP is present in a protein other than ASP.

Database searching reveals significant homology between the C-terminal portion of the ASP deduced amino acid sequence, approximately 230 amino acids, and the antigen 5 molecule of Hymenoptera venoms.

Antibodies against the antigen 5 of the yellow jacket *Vespula squarnosa* recognize a 40 kDa protein in activated, but not in non-activated, *A. caninum* $L_3$ excretory/secretory (ES) products. Additionally, this antibody recognizes a 38 kDa protein in lysates of bacteria that are expressing a one kilobase 3'-end fragment of the ASP cDNA, but not in uninduced bacteria. The anti-antigen 5 antibody recognizes bands of slightly higher molecular weight, approximately 42 kDa, in soluble extracts of *A. caninum* adults and $L_3$ and *A. braziliense*, *Haemonchus contortus*, and *Strongyloides stercoralis* $L_3$. The size difference is due to the presence of the 18 amino acid eukaryotic secretory signal peptide of ASP in the unsecreted form.

DNA Encoding Aacylostoma Secreted Protein

A cDNA molecule encoding ASP has the nucleotide sequence listed as SEQ ID NO:1. The coding region in this sequence is 1272 nucleotides long. The coding region for mature ASP begins at nucleotide 55 and ends at nucleotide 1272. Unless otherwise stated, all nucleotide position references use the numbering shown in SEQ ID NO:1. As used herein, a nucleic acid molecule encoding ASP refers to a nucleic acid molecule encoding a protein having the amino acid sequence shown in SEQ ID NO360:2 from amino acid 19 to amino acid 424; derivatives thereof with conservative amino acid substitutions, deletions, or additions; any homolog or allelic form of ASP produced in nematodes; any protein having at least 40% amino acid sequence identity with amino acids 19 to 424 of SEQ ID NO:2; or any protein that is immunoreactive with an antibody immunoreactive with the ASP of SEQ ID NO:2 but that is not immunoreactive with hymenoptera proteins. Preferred the encoded ASP derivatives have an amino acid sequence identity with amino acids 19 to 424 of SEQ ID NO:2 of greater than 40%, such as at least 50% amino acid sequence identity, at least 60% amino acid sequence identity, or at least 70% amino acid sequence identity. Preferably, the encoded ASP derivatives have at least 80% amino acid sequence identity; more preferably, at least 90% amino acid sequence identity; and most preferably, at least 95% amino acid sequence identity with amino acids 19 to 424 of SEQ ID NO:2. Amino acid sequence identity and immunoreactivity of the encoded protein are determined as described earlier.

Nucleic acid molecules encoding all or a part of ASP can be manipulated using any of the numerous nucleic acid manipulation methods known to those of skill in the art. Such manipulation include amplification, purification, recombination, insertion into vectors, and use as probes, consisting of at least 14 to 17 nucleotides, and primers.

A. Recombinant ASP

ASP can be made recombinantly using any of the established expression systems, such as bacteria, yeast, baculovirus, and mammalian cell culture. As used herein, recombinant refers to any protein or nucleic acid produced by any methods within the large body of well known nucleic acid manipulations, examples of which are provided below. As used herein, any protein or nucleic acid that results from, or is expressed from a nucleic acid resulting from, such manipulations is a recombinantly produced protein or nucleic acid.

Recombinant expression allows the production of fragments of ASP, combinations of ASP fragments in a single fusion protein, and fusion proteins combining ASP, or a fragment of ASP, with one or more other proteins or amino acid sequences. Such fusions are useful for combining multiple immunogenic fragments in a single protein.

The DNA used to produce ASP may be genomic DNA, in which case it may include introns, or it may be cDNA which is prepared in vitro from mRNA using a reverse transcriptase and which contains open reading frames. Methods for isolation, cloning or synthesizing DNA and cDNA are well known to those of skill in the art. Expression refers to the process by which nucleic acid is transcribed and translated into peptides, polypeptides, or proteins. If the nucleic acid is derived from genomic DNA, expression may, if an appropriate eukaryotic host cell or organism is selected, include splicing of the mRNA. An expression vector refers to a recombinant DNA or RNA construct, such as a plasmid, a phage, recombinant virus or other vector that, upon introduction into appropriate host cells, causes nucleic acid molecules that have been cloned into the vector to be transcribed, and then translation of the transcribed nucleic acid into a polypeptide. The nucleic acid molecule is cloned into the vector in such a manner that it is operably linked to regulatory sequences that effect expression of the heterologous nucleic acid molecules. Upon expression in a selected host cell or organism, if the appropriate regulatory sequences are operably linked to the DNA or included in the heterologous DNA, the expression product may be exported to the cytoplasm and/or may be secreted out of the host cell.

Appropriate expression vectors are well-known to those of skill in the art and include those that are replicable in eukaryotic cells and/or prokaryotic cells. Such expression vectors may remain episomal or may integrate into the host cell genome.

In all cases, the ASP cDNA or gene can be inserted into appropriate expression vectors containing expression regulatory elements, such as transcription initiation signals, translation initiation signals, starting codon, termination codon, transcription terminating signals, polyadenylation signals, and others. Suitable vectors are commercially available from a variety of companies. After the recombinant vectors containing ASP-encoding DNA are transfected into the host cells, they may remain as extrachromosomal DNA or they may be integrated into the host genome. In either case, they may direct the synthesis of recombinant ASP in the host cells. Some examples for the expression of heterologous genes are described in *Methods in Enzymology*, Vol. 153, Chapters 23 to 34 (Wu and Grossman, eds., Academic Press, 1987). Large scale culture of the ASP synthesizing host cells and the purification of the enzyme may form a cost effective commercial means of production of ASP. Methods are well known to those skilled in the art for the large scale production of proteins. Many methods and reagents useful for recombinant expression of ASP are described in *The 1995 Lab Manual Source Book* (Cold Spring Harbor Laboratory Press, NY, 1995).

Some examples of potentially useful expression systems for ASP are given below:

1. *E. coli* or other bacteria as host: Many mammalian cDNA's have been expressed in *E. coli* and many expression vectors with different promoters, operators, and other regulatory elements are available commercially. A typical vector construction and expression is described by Lin and Tang, *J. Biol. Chem.* 264: 4482–4489 (1989). The expression of some eukaryotic proteins in the cytosol of *E. coli* produces insoluble 'inclusion bodies' and would require the refolding of recombinant protein. However, the use of a 'leader' sequence, such as omp, described by Duffaud et al. in *Methods in Enzymology* 153: 492–506 (Wu and Grossman, eds., Academic Press, 1987), will direct the proper folding and also export of the recombinant ASP to the periplasmic space of the bacterial.

2. Yeast as host: The principles for the expression of recombinant ASP in the yeast are similar to those for *E. coli* expression. Examples are provided by Bitter et al. in *Methods in Enzymology* 153: 516–544 (Wu and Grossman, eds., Academic Press, 1987). Like *E. coli*, yeast host cells may express a foreign gene either in the cytosol or as secreted protein.

3. Fungi as host: There are small numbers of fungal expression vectors which have been successfully used to express heterologous genes. The existing fungal expression vectors integrate themselves into the host genome after transfection as indicated by Cullen et al., in *A Survey of Molecular Cloning Vectors and their Uses*, (Butterworth Publishers, Stoneham, MA 1986). When a leader is present in front of the expressed protein codons, the secreted recombinant proteins can be glycosylated. Some examples of successful expressions involve bovine chymosin, described by Cullen et al., *Bio/Technology* 5: 369–378 (1987), and an acid protease from a different fungus, described by Gray et al., *Gene* 48: 41–53 (1987).

4. Insect cells as host: Baculovirus expression vectors for the synthesis of foreign genes in insect cells have been successfully used to express many eukaryotic and viral proteins. This system is capable of glycosylation, if the protein has glycosylation sites, and can also express recombinant proteins at a high level. The use of this system has been reviewed in some detail by Luckow and Summers, *Bio/Technology*, Sep. 11, 1987. The recombinant ASP fusion proteins can also be expressed in insect cells using other expression vectors such as Entomopox viruses and cytoplasmic polyhedrosis viruses (CPV).

5. Mammalian cells as host: Many heterologous genes have been expressed in mammalian cells on a commercial scale. The commercial production of recombinant human tissue plasminogen activator is an example. Most of these expression vectors contain 1) either a mammalian promoter, such as metallocyanin or growth hormone, or viral promoters, such as SV40 early promoter or long terminal repeats of viral genes; 2) polyadenylation signals; and 3) appropriate regulatory elements for *E. coli* cloning including antibiotic resistance genes. After the insertion of ASP downstream from the promoter, the vector can be first cloned in *E. coli*, isolated and transfected into mammalian cells. Neomycin or similar resistant selection markers can be either cotransfected in another vector or in the same vector. For high level expression, a gene amplification system is advantageous. For example, the expression vector can contain the gene of dihydrofolate reductase (dhfr). When the dhfr-strain of Chinese hamster ovary (CHO) cells are used, the cloned gene can be coamplified with that of dhfr by adapting the transformed cells to increasing methotrexate concentration. The transformant clones secreting ASP can be identified by enzyme assays or by western blots. Successful examples of this approach include the synthesis of recombinant prorenin, described by Poorman et al., *Proteins* 1: 139–145 (1986), and human immune interferon, described by Scahill et al., *Proc. Natl. Acad. Sci., U.S.A.* 80: 4654–4658 (1983).

B. Purification of Recombinant ASP.

Methods for purifying proteins are well known and can be generally divided into chromatographic methods, for example, ion exchange chromatography, molecular weight sieving, high pressure liquid chromatography, affinity chromatography, and electrophoretic methods, for example, electrophoresis on agarose or acrylamide gels and isoelectric focusing. Any of these methods can be adapted to purify ASP.

A preferred method of purification is affinity chromatography. In immunoaffinity chromatography, an antibody to ASP is immobilized on a chromatographic substrate, a mixture containing ASP is applied to the substrate under conditions allowing the antibody to bind ASP, the unbound material is removed by washing, and the bound ASP is eluted using, for example, high or low pH, protein denaturants or chaotropes.

For example, ASP may be purified by affinity chromatography using one or a combination of immobilized antibodies such as those described below covalently bound to agarose beads or bound non-covalently via a Goat-anti mouse IgM antibody to *Staphylococcus aureus* protein G beads. ASP isolation can also be achieved, for example, by incubating cell extracts with an anti-ASP antibodies, described below, attached to a solid phase, such as chemical conjugation to agarose beads. After incubation, the beads are washed, denatured and resolved on a polyacrylamide gel.

HOOKWORM VACCINES

ASP or immunogenic fragments of ASP can be formulated and packaged using methods and materials known to those skilled in the art of vaccines, examples of which are described below. As used herein, an immunogenic fragment of a protein is a protein fragment of at least five to eight amino acids that elicits an immune response in an animal or individual. For use in a vaccine, ASP or immunogenic fragments of ASP can be fused to one or more other proteins or amino acid sequences. Such fusions are useful for combining multiple antigens in a single vaccine.

A. Carriers

Numerous carriers for administration of vaccine compounds are known. These include simple liquid carriers, adjuvants, and polymeric and lipid compositions. Simple liquid carriers, such as water or a buffered saline, can be used; either alone or in combination with other carriers.

1. Adjuvants: For administration as a vaccine, ASP can be combined with an adjuvant, in an amount effective to enhance the immunogenic response. A common adjuvant widely used in humans is alum, that is, aluminum phosphate or aluminum hydroxide. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, and phospholipid conjugates such as those described by Goodman-Snitkoff et al., *J. Immunol.* 147: 410–415 (1991), and incorporated by reference herein, can also be used. A preferred adjuvant is Syntex Adjuvant Formulation (SAF), which is described by Allison and Byars, *J. Immunol. Methods* 95: 157 (1986), and Byars and Allison, *Vaccine* 5: 223 (1987).

Adjuvants for oral administration.

It is known that oral administration of an admixture of trace amounts of cholera toxin (CT), either cholera toxin subunit A, cholera toxin subunit B, or both, and a second antigen stimulate a mucosal immunity to the co-administered antigen. Furthermore, there is a dramatic humoral immune response to the second antigen instead of the immune tolerance that is elicited by oral delivery of the antigen alone. Thus, mucosally delivered CT functions as a powerful immunostimulant or adjuvant of both mucosal and humoral immunity. It is therefore preferred to enhance immunogenicity of the orally administered antigen by including CT in the vaccine.

Adjuvants for parenteral administration.

Examples of adjuvants include muramyl dipeptides, muramyl tripeptide, cytokines, diphtheria toxin, and exotoxin A. Commercially available adjuvants include QS-21 from Cambridge Biosciences, Worcester, MA, and monophosphoryl lipid A (MPLA) from Ribi Immunochem.

2. Polymeric Carriers: The carrier may also be a polymeric delayed release system. Synthetic polymers are particularly useful in the formulation of a vaccine to effect the controlled release of antigens. An example of this is described by Kreuter, *Microcapsules and Nanoparticles in Medicine and Pharmacology*, pages 125–148 (M. Donbrow, ed., CRC Press). The use of other particles have demonstrated that the adjuvant effect of these polymers depends on particle size and hydrophobicity.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters, and polyamides, particularly those that are biodegradable.

A frequent choice of a carrier for pharmaceuticals and more recently for antigens is poly (d,l-lactide-co-glycolide) (PLGA). This is a biodegradable polyester that has a long history of medical use in erodible sutures, bone plates and other temporary prostheses, where it has exhibited no toxicity. A wide variety of pharmaceuticals including peptides and antigens have been formulated into PLGA microcapsules. A body of data has accumulated on the adaptation of PLGA for the controlled release of antigen, for example, as reviewed by Eldridge et al., *Current Topics in Microbiology and Immunology* 146: 59–66 (1989). The PLGA microencapsulation process uses a phase separation of a water-in-oil emulsion. In this process, ASP is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

3. Proteosome Carriers: Proteosomes, combinations of protein and liposomes, can also be used as carriers for ASP; using ASP as the protein component. The procedures and materials for the use of proteosomes are as described in Lowell et al., *Science* 240:800 (1988); Lowell, in *New Generation Vaccines* (Woodrow and Levine, eds., Marcel Dekker, NY, 1990), Ch. 12, pages 141–160; and Orr et al., *Infect. Immun.* 61: 2390 (1993), the teachings of which are incorporated herein.

It will be understood by those skilled in the art that the immunogenic vaccine composition can contain other physiologically acceptable ingredients such as water, saline or a mineral oil such as Drakeol™, Markol™, and squalene, to form an emulsion, or in combination with aqueous buffers, or encapsulated within a capsule or enteric coating to protect the protein from degradation while passing through the stomach.

B. Nucleic Acid Vaccines

Nucleic acid encoding all or an immunogenic part of ASP can also be used as or in a vaccine. For example, a benign microorganism expressing ASP can be administered as a vaccine. A vaccine of this type is described by Eisinstein, *Science* 214: 337–338 (1981). Nucleic acid encoding ASP can also be directly administered, in the manner described by Liu et al., *AIDS Research and Human Retroviruses* 10: S34 (1994), and Donnelly et al., *J. Immunol. Methods* 176(2): 145–152 (1994).

Administration of Vaccine

In a preferred embodiment, the vaccine is packaged in a single dosage for immunization by parenteral, that is, intramuscular, intradermal or subcutaneous, administration; or nasopharyngeal, that is, intranasal, administration. The effective dosage is determined using standard techniques, such as antibody titer. The antigen may be lyophilized for resuspension at the time of administration or in solution. If administered with adjuvant, the adjuvant may be administered in combination with or in the vicinity of the vaccine.

Immunity can be measured using assays to detect and quantitate antibodies that bind to ASP. Cellular immunity can be measured using assays that measure specific T-cell responses such as delayed type hypersensitivity (DTH) and lymphocyte proliferation.

The dosage is determined by the antigen loading and by standard techniques for determining dosage and schedules for administration for each antigen, based on titer of antibody elicited by the antigen administration. As used herein, a dose effective to elicit an immune response is considered to be one that causes antibody titer to increase compared to untreated animals or individuals, using any of the known methods of titering antibodies.

As an example of ASP vaccine use in animals, and to test the use of ASP as a vaccine, the following procedure can be used. Dogs in the experimental group can be immunized with 0.2 mg of recombinant ASP in the presence of an equal volume of aluminum hydroxide (alum). The initial injection can be performed at an intramuscular (i.m.) site. For testing efficacy, control dogs can be injected with alum alone. Boosts can be administered over two week intervals. The first boost can also use 0.2 mg recombinant ASP injected i.m. in the presence of an alum adjuvant, while the second boost can use 0.1 mg of recombinant ASP in buffer administered by the intravenous route.

Circulating antibodies to recombinant ASP can be detected by enzyme immunoassay using recombinant ASP as antigen. Such assays are described below. Briefly, plates can be coated with 1 microgram of recombinant ASP per well. Horse radish peroxidase (HRP)-conjugated goat anti-dog IgG antibodies is used at 1:1,000 dilution. Canine immune responses can also be measured by immunofluorescence (IFA), two-direction agarose diffusion and by Western/immunoblotting as described by Liu Shu-xian et al., *SE Asian J. Trop. Med. Pub. Health* 24: 61–65 (1993).

Following immunization both experimental and control groups of dogs can be challenged with 500 *A. caninum* infective larvae. The natural history of these hookworm infections will be monitored by following a number of biological parameters including 1) numbers of gastrointestinal tract, 2) parasite wet weight (size), 3) quantitative egg counts in order to examine parasite fecundity, 4) circulating hemoglobin concentrations and hematocrits to measure the extent of hookworm anemia, 5) circulating total protein and albumin concentration, and 6) measurement of ASP and ASP nucleic acid levels.

Diagnostics

Detection and quantitation of ASP, hookworm nucleic acid, and anti-ASP antibodies in clinical samples and body fluids can be accomplished using any of the known methods for detection of antigens, nucleic acids, and antibodies. Such assay are useful for determining if an individual is infected with hookworm, whether an individual is producing hookworm antibodies, and for testing the concentration or potency of ASP vaccines or ASP antibodies.

A. Antibodies

Many useful assays involve the use of antibodies specific for ASP protein. Such antibodies can be made using any of the known procedures, examples of which are described below. As used herein, an antibody specific for ASP protein is an antibody that is immunoreactive with an ASP protein, as defined herein, but that is not immunoreactive with hymenoptera proteins.

1. In vivo Immunization of Mice: Animals such as mice may be immunized by administration of an amount of ASP, or a fragment of ASP, effective to produce an immune response. Preferably a mouse is subcutaneously injected in the back with 100 micrograms of antigen, followed three weeks later with an intraperitoneal injection of 100 micrograms of ASP with adjuvant, most preferably Freund's complete adjuvant. Additional intraperitoneal injections every two weeks with adjuvant, preferably Freund's incomplete adjuvant, may be necessary until the proper titer in the mouse's blood is achieved. In order to use the mice for fusion and hybridoma production, a titer of at least 1:5000 is preferred, and a titer of 1:100,000 or more is most preferred.

2. In vivo Immunization of Rabbits: Rabbits may be immunized by administration of ASP, or a fragment of ASP, effective to produce an immune response. Preferably a rabbit is intradermally and intravascularly injected at multiple sites with an adjuvant, preferably Freund's complete adjuvant, and ASP coupled to a carrier.

3. In vitro Immunization: *In vitro* immunization of human lymphocytes can be used to generate human monoclonal antibodies (MAb) to ASP. Techniques for *in vitro* immunization of human lymphocytes are well known to those skilled in the art. Examples of this method are described by Inai et al., *Histochemistry* (Germany) 99(5): 335–362 (May 1993); Mulder et al., *Hum. Immunol.* 36(3): 186–192 (Mar. 1993); Harada et al., *J. Oral Pathol. Med.* (Denmark) 22(4): 145–152 (Apr. 1993); Stauber et al., *J. Immunol. Methods* (Netherlands) 161(2): 157–168 (May 26, 1993); and Venkateswaran et al., *Hybridoma* 11(6): 729–739 (Dec. 1992), which are incorporated herein by reference. These techniques can be used to produce antigen-reactive human monoclonal antibodies, including antigen-specific IgG, and IgM human monoclonal antibodies.

4. Monoclonal Antibodies: Standard monoclonal antibody technology, described by Galfré and Milstein, *Methods Enzymol.* 73: 3–46 (1981), can be used to obtain anti-ASP MAbs. Briefly, MAbs to ASP can be produced after immunization of mice with purified ASP or a fragment of ASP. Hybridomas are produced using spleen cells from mice immunized with the antigen. The spleen cells of each immunized mouse is fused with mouse myeloma Sp 2/0 cells, for example using the polyethylene glycol fusion method described by Galfré and Milstein (1981). Growth of hybridomas, selection in HAT medium, cloning and screening of clones against antigens are carried out using standard methodology described by Galfré and Milstein (1981).

HAT-selected clones are injected into mice to produce large quantities of MAb in ascites, as described by Galfréand Milstein (1981), and the MAbs in ascites may then, if desired, be purified using protein A column chromatography. MAbs are selected on the basis of their (a) specificity for ASP, (b) high binding affinity, (c) isotype, and (d) stability.

C. Purification of Antibodies

Several standard methods of antibody purification are known in the art. Any of these is suitable to purify ASP antibodies. For example, ASP antibodies can be purified by affinity chromatography using antigen molecules immobilized on a solid support.

D. Labelled Antibodies

Anti-ASP antibodies can be directly or indirectly labelled with a detectable label to facilitate detection of the presence of the antibodies by detection of the label. Various types of labels and methods of labelling antibodies are well known to those skilled in the art. For example, the antibody can be labelled directly or indirectly with a radiolabel such as, but not restricted to, $^{32}P$, $^{3}H$, $^{14}C$, $^{35}S$, $^{125}I$, or $^{131}I$. The radiolabel is generally attached by chemical modification. Detection of a label can be by methods such as scintillation counting, gamma ray spectrometry or autoradiography.

Fluorogens can also be used directly or indirectly to label the anti-ASP antibodies. Examples of fluorogens include fluorescein and derivatives, phycoerythrin, allophycocyanin, phycocyanin, rhodamine, or Texas Red. The fluorogens are generally attached by chemical modification and can be detected by a fluorescence detector.

The anti-ASP antibody can alternatively be labelled directly or indirectly with a chromogen to provide an enzyme or affinity label. For example, the antibody can be biotinylated so that it can be utilized in a biotin-avidin reaction which may also be coupled to a label such as an enzyme or fluorogen. For example the antibody can be labelled with peroxidase, alkaline phosphatase or other enzymes giving a chromogenic or fluorogenic reaction upon addition of substrate. Additives such as 5-amino-2,3-dihydro-1,4-phthalazinedione, also known as Luminol™ (Sigma Chemical Company, St. Louis, Mo.), and rate enhancers such as p-hydroxybiphenyl, also known as p-phenylphenol (Sigma Chemical Company, St. Louis, Mo.), can be used to amplify enzymes such as horseradish peroxidase through a luminescent reaction; and luminogeneic or fluorogenic dioxetane derivatives of enzyme substrates can also be used. Such labels can be detected using enzyme-linked immunosorbent assays (ELISA) or by detecting a color change with the aid of a spectrophotometer.

E. Testing for Specificity and Affinity

Anti-ASP antibodies can be screened or tested for specificity using any of a variety of standard techniques, including Western Blotting and ELISA, both described by Koren et al., *Biochim. Biophys.*, Acta 876: 91–100 (1986). Many assays useful for determining immunoreactivity and specificity are described in Johnstone and Thorpe, *Immunochemistry in Practice*, Second edition (Blackwell Scientific Publication, Oxford, 1987). For example, in ELISA, separate wells in microtiter plates are coated with purified ASP which adsorb to the wall of the wells. The wells are then treated with a blocking agent, such as bovine serum albumin or nonfat milk proteins, to cover areas in the wells not bound by antigen. Ascites fluid or other antibody-containing preparation can then be applied to each well in varying concentrations and adequate time allowed for antibody to bind the antigen adsorbed on the wall of each well. The presence of antibody bound to antigen in a well can then be detected using a standard enzyme-conjugated anti-mouse antibody which will bind antibody that has bound to ASP in the well. Wells in which antibody is bound to antigen are then identified by adding a chromogenic substrate for the enzyme conjugated to the anti-antibody antibody and color production detected by an optical device such as ELISA plate reader.

Antibodies that bind to a particular ASP fragment with no reactivity with other ASP regions are considered specific for that fragment. To determine specificity of MAbs for a particular ASP fragment individual wells on ELISA plates are coated with various ASP fragments and subjected to the identical procedure. To determine whether or not two antibodies specific for the same ASP fragments bind to different epitopes, a competitive ELISA is carried out as follows. For example, one of the antibodies is biotinylated whereas the other is not so modified. Mixtures containing a constant concentration of the biotinylated antibody and increasing concentrations of the non-biotinylated antibody are incubated with wells coated with the appropriate ASP fragment. The quantity of biotinylated antibody bound to the coated antigen is determined using a streptavidin-peroxidase conjugate and a chromogenic substrate. A decreased binding of the biotinylated antibody with increasing concentrations of the non-biotinylated antibody indicates that the two antibodies compete for the same epitope. If the biotinylated antibody binds equally to the antigen despite increasing concentrations of the non-biotinylated antibody, the two antibodies do not compete for the same epitope. This competition can be complete or partial.

Affinity of antibodies can be determined using radioactively labelled ($^{125}I$) ASP and purified antibodies as described previously by Koren et al., (1986).

F. Antibodies and ASP Immobilized on Solid Phase Materials

1. Solid Phase Materials: Antibodies and ASP can be bound to a solid phase material for use in assays described herein. Various types of adsorptive materials, such as nitrocellulose, Immobilon™, polyvinyldiene difluoride (all from BioRad, Hercules, calif.) can be used as a solid phase material in the compositions and methods described herein. Pieces or strips of these materials can be coated with one or more antibodies, or functional fragments thereof, directed against specific epitopes of ASP; or with ASP, for detection of anti-ASP antibodies. Such strips are referred to herein as "dipsticks". The strips may also be attached to one end of a longer strip of a solid support material, such as plastic, which can serve as a handle for dipping the dipstick into various solutions and samples. The plastic handle can also serve as a tether so that multiple dipsticks can be attached to a common support. Such a multi-strip design may be particularly useful in screening for different forms of ASP simultaneously.

Although various sizes of dipsticks are possible, typically, pieces of the solid phase material that are coated with antibody have the general dimensions of 0.5 cm×0.5 cm and can be attached to the longer solid support strips having general dimensions of 0.5 cm×5 cm. Such dimensions permit an accurate determination of ASP levels in as little as 100 μl of blood.

2. Coating solid phase material with antibodies and ASP: The solid phase material may be coated with antibodies or ASP by any of a variety of methods. If the material is made of a protein-receptive solid phase material that adsorbs proteins, such as nitrocellulose or polyvinyldiene difluoride (PVDF) membrane, the material can be coated directly with antibody or ASP by immersing the solid phase material directly into a solution of the protein.

After protein has been adsorbed on the material, the material is treated ("blocked") with a blocking agent in order to minimize nonspecific adsorption of proteins to unoccupied domains on the material. The solid phase material can be treated with any of a variety of blocking agents such as bovine serum albumin (BSA), gelatin, Tris, all of which are available commercially (Sigma, St Louis, Mo.) or nonfat milk proteins. For example, PVDF strips can be blocked with two percent (w/v) milk blocking solution (Kirkegaard and Perry Laboratories, Gaithersburg, Md.) for 48 hours at 4° C.

A dipstick may be coated with more than one antibody or ASP so that the single dipstick can be used to detect more than one anti-ASP antibody or more than one form of ASP. For example, two or more separate pieces of a solid phase material, each coated with an antibody directed against a particular ASP or ASP fragment, can be attached (for example, by gluing) to a longer strip of solid support to produce a dipstick with two or more separate areas.

G. Detection of ASP

ASP can be detected and quantitated using any of the known methods of protein detection. Examples include radioimmunoassays (RIA), Western Blotting (Koren et al. (1986)) and enzyme-linked immunosorbent assay (ELISA) (Koren et al. (1986)). Many assays useful for detection of ASP are described in Johnstone and Thorpe, *Immunochemistry in Practice*, Second edition (Blackwell Scientific Publication, Oxford, 1987). Preferred assays use the ASP-specific antibodies and antibody compositions described above. All of the antibody assays involve bringing into contact a sample to be tested and an antibody that recognizes an Ancylostoma Secreted Protein under conditions promoting conjugation of an Ancylostoma Secreted Protein and the antibody. The bound antibody is then detected, and, depending on the assay, quantitated. Detection and quantitation is typically facilitated by using labelled antibody as described above. Detection of a radiolabel can be by methods such as scintillation counting, gamma ray spectrometry or autoradiography. Fluorogens can be detected by a fluorescence detector. Antibodies directly or indirectly labelled with chromogens are detected visually or spectrophotometrically. Such by detection is preceded by an enzymatic development step when using some chromogens.

H. Detection of Antibodies to ASP

Antibodies that recognize ASP can be detected and quantitated using any of the known methods of antibody detection. Examples include dot blot assays and ELISA. Detection of antibodies that recognize ASP is useful for determining if an individual has ever been infected with hookworm and to evaluate antibody preps. Detection of these antibodies involves bringing into contact a sample to be tested and ASP or an immunogenic part of ASP under conditions promoting conjugation of antibody and ASP. The bound protein is then detected, and, depending on the assay, quantitated. Detection and quantitation is typically facilitated by using labelled protein.

ASP can be used in solution or immobilized to a solid substrate, such as a gel suitable for affinity chromatography, or a multi-well plate, using standard techniques known to those skilled in the art.

To facilitate detection and quantitation, the peptides can be labelled using standard techniques, for use in routine assays, with radioactive, fluorescent, or enzyme labels. Detection of a radiolabel can be by methods such as scintillation counting, gamma ray spectrometry or autoradiography. Fluorogens can be detected by a fluorescence detector. Proteins directly or indirectly labelled with chromogens are detected visually or spectrophoto-metrically. Such by detection is preceded by an enzymatic development step when using some chromogens.

An advantage of the cloned antigens is the ease of preparation of the antigen for use in ELISA. ELISA has advantages over other techniques for quantitation of antibody, which can be used to determine antibody titer. The cloned antigen can also be used to simplify detection of the antigen in a dot blot assay, which cannot be done with whole extract. A dot blot assay can be modified to a "dip-stick" type of test to make it even more simple and incorporate it into a test for multiple specificities at once.

I. Detection of hookworm nucleic acid: Nucleic acid molecules encoding all or a part of ASP can be performed using any of the many well known nucleic acid detection methods. Nucleic acid hybridization assays generally involve bringing into contact a sample to be tested and a labelled nucleic acid probe encoding ASP under conditions promoting hybridization of nucleic acid molecules. The bound nucleic acid is then detected, and, depending on the assay, quantitated.

The detectable portion of the bound probe has traditionally been a substance chemically affixed to the probe such as a chemical label. Examples of chemical labels are radioisotopes, substrate-modifying enzymes such as alkaline phosphatase, enzymatic cascade processes utilizing NADP, and fluorescent compounds. Assays utilizing nucleic acid probes, to which a chemical label has been attached, are described by Grunstein et al., *Proc. Natl. Acad. Sci. USA* 72: 3961 (1975) and Southern, *J. Mol. Biol.* 98: 503 (1975), and in U.S. Pat. No. 4,851,331 to Vary et al.; U.S. Pat. No. 4,581,333 to Kourilsky et al.; U.S. Pat. No. 4,994,373 to Stavrianopoulos et al.; U.S. Pat. No. 4,882,269 to Schneider et al.; and International Patent Application Publication No. WO87/03622 to Princeton University.

Recent probe technology has utilized signal-amplification systems that amplify the signal for detection of smaller quantities of target molecule. For example, in nucleic acid assays, the polymerase chain reaction (PCR) and similar processes are used to increase the number of copies of the target molecule to which the detectable probe will bind.

PCR has emerged as a powerful and sensitive procedure for the amplification of specific DNA sequences, and is a valuable tool in paternity identification, tissue typing, and forensics. PCR technology requires pairs of dissimilar DNA oligonucleotides that act as primers to initiate a controlled polymerase reaction for amplification of the DNA sequence that lies between the two oligonucleotide binding sites. The polymerase chain reaction employs the heat-stable Taq polymerase that permits repeated heating and cooling of the reaction mixture. The amplification process is initiated by first heating the reaction mixture to denature, or dissociate, the two complementary strands of the double-stranded DNA to be amplified. Upon cooling, each single-stranded DNA oligonucleotide hybridizes to a specific region of one or the other of the complementary DNA strands and acts as a primer for the heat-stable polymerase. The polymerase uses the oligonucleotide primers as starting points for the elongation of a DNA molecule complementary to the template DNA molecule to which each primer is hybridized. Each of the elongating DNA chains grows towards and beyond the distal primer site of the other template strand. By the end of the first cycle, two double-stranded copies of the intervening genomic sequence lying between the primer binding sites are generated. The cycle is repeated many times, exponentially doubling the number of copies each time. In this way, even a single copy of a specific DNA sequence can be amplified to detectable levels in a relatively short period of time.

PCR technology is described in U.S. Pat. No. 4,683,202 to Mullis; U.S. Pat. Nos. 4,683,195 and 4,965,188 to Mullis et al.; and International Pat. Application Publication No. WO92/14843 to Gilead Sciences Inc.

Other assays employing the concept of signal amplification utilize DNA-dependent RNA polymerases for the amplification of portions of either the target molecules or probe molecules bound to target molecules. In this type of signal amplification assay, an RNA polymerase promoter sequence is included as part of a single-stranded DNA probe so that, after hybridization of the probe to the target, the promoter can be used to promote polymerase-catalyzed synthesis of target or probe segments. Assays employing DNA transcription-based amplification systems are described by Kwoh et al., *Proc. Natl. Acad. Sci. USA* 86: 1173–1177 (1989); Guarelli et al., *Proc. Natl. Acad. Sci. USA* 87: 1874–1878 (1990); Japanese Patent Application No. 2,131,599 to Toray Ind. Inc.; International Patent Application Publication No. WO91/17442 to Chiron Corp.; International Patent Application Publication No. WO91/10746 to Chiron Corp.; and International Patent Application Publication No. WO89/06700 to Genentech, Inc.

In a similar RNA based amplification system, a nucleic acid probe containing an RNA molecule is autocatalytically replicated using Qβ bacteriophage replicase as described by Chu et al., *Nucl. Acids Res.* 14: 5591–5603 (1986); U.S. Pat. No. 4,957,858 to Chu et al.; U.S. Pat. No. 4,786,600 to Kramer et al.; and International Pat. Application No. WO92/12261 to Promega Corp.

Probes have been indirectly labelled in an attempt to avoid the problems associated with direct radioactive labelling. The most common method of indirect labelling is to attach biotin, a small vitamin, to the nucleic acid using a chemical or enzymatic technique. Following hybridization, the biotin is detected by reaction with avidin, an egg white protein which has been labelled with an enzyme or fluorochrome. Bound enzyme can be detected by reaction with color-producing substrates and the fluorochrome can be seen when reacted with incident light of appropriate wavelength.

Hybridization has been detected with the use of an intercalating agent such as acridine orange or ethidium bromide as described in U.S. Pat. No. 4,563,417 to Albarella et al. The intercalating agent becomes inserted between hybridized base pairs of probe and sample nucleic acids and causes the tertiary structure of the helix to unwind. An antibody specific for the newly formed antigenic determinant created by the intercalating agent and the unwound helix is detected by conventional means.

Hybridization can also be detected with the aid of an antibody specific for a labelled probe as described in U.S. Pat. No. 4,743,535 to Carrico. The probe is labelled with a detectable substance such as flavin adenine dinucleotide (FAD) or a fluorescent agent. An antibody specific for the labelled probe, after it has hybridized to the sample nucleic acid, is detected by a biochemical reaction.

Monoclonal antibodies to DNA-RNA hybrids are now available. U.S. Pat. No. 4,732,847 to Stuart et al. and the publication of Stuart et al., *Proc. Natl. Acad. Sci., USA* 78: 3751 (1981) describe a method of hybridization detection involving a monoclonal antibody specific for a poly(A)-poly (dT) duplex. A monoclonal antibody specific for DNA-RNA hybrids, secreted by hybridoma HB 8730, is disclosed in U.S. Pat. No. 4,833,084 to Carrico et al. Boguslawski et al., *J. Immunuol. Methods* 89: 123–130 (1986) developed a hybridization assay using anti-hybrid coated polystyrene beads isolated on filter paper in an attempt to reduce non-specific binding and avoid complicated washing procedures.

Targeting of Therapeutics

Therapeutics that can bind to, and inhibit the effect of, ASP during hookworm infection can be designed. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. Methods for generating this data and determining three-dimensional structure of a protein are known to those of skill in the art. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modelling systems are the CHARMm and QUANTA programs, Polygen Corporation, Waltham, MA. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159–166; Ripka, *New Scientist* 54–57 (Jun. 16, 1988); McKinaly and Rossmann, 1989 *Annu. Rev. Pharmacol. Toxiciol.* 29, 111–122; Perry and Davies, *QSAR: Quantitative Structure-Activity Relationships in Drug Design* pp. 189–193 (Alan R. Liss, Inc. 1989); and Lewis and Dean, 1989 *Proc. R. Soc. Lond.* 236, 125–140 and 141–162. Other computer programs that screen and graphically depict chemicals are available from companies such as BioDesign, Inc., Pasadena, CA., Allelix, Inc, Mississauga, Ontario, Canada, and Hypercube, Inc., Cambridge, Ontario. Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which bind to ASP.

The present invention will be further understood by reference to the following non-limiting examples.

EXAMPLE 1

CLONING OF ASP.

Materials and Methods

Larval Activation:

*Ancylostoma caninum* was maintained as described previously by Hawdon and Schad, *Experimental Parasitology* 77: 489–491 (1993), and Schad, in *Aspects of Parasitology: A Festschrift Dedicated to the Fiftieth Anniversary of the Institute of Parasitology of McGill University* (Meerovitch, ed., McGill University, Montreal, 1982), pages 361–391). $L_3$ were collected from one to four week old coprocultures by the Baermann technique, and decontaminated with 1% HCl in BU buffer (50 mM $Na_2HPO_4$/22 mM $KH_2PO_4$/70 mM NaCl, pH 6.8) (Hawdon and Schad, *Journal of the Helminthological Society of Washington* 58: 140–142 (1991)) for 30 minutes at 22° C. Approximately 3500–7500 $L_3$ were "activated" by incubation in 0.5 mL RPMI1640 tissue culture medium (supplemented with 0.25 mM HEPES pH 7.2, 100 U/mL penicillin, 100 µg/mL streptomycin, 100 µg/mL gentamicin, and 2.5 µg/mL amphotericin B) containing 15% (v/v) of a less than 10 kDa filtrate of canine serum (FIL) (Hawdon et al. (1995)) and 25 mM GSM in individual wells of 12 well tissue culture plates. Non-activated $L_3$ were incubated in RPMI alone. The larvae were incubated at 37° C., 5% $CO_2$ for 24 hours.

Collection of ES products:

Media containing activated larvae was transferred to individual microfuge tubes and centrifuged for 5 minutes at 16,000 rpm. The tubes were placed on ice for 10 minutes to slow the swimming motions of the larvae. The supernatant containing the ES products was carefully transferred to a new microfuge tube, and inspected visually using a dissection microscope to assure that no $L_3$ had been transferred. The supernatants were pooled and stored at −20° C. Prior to electrophoresis, supernatants are concentrated four to ten fold by lyophilization or ultrafiltration using Centricon™10 cartridges (Amicon).

Protein Sequencing:

ES products from approximately 50,000 activated A. caninum $L_3$ were concentrated and electrophoresed in a 12.5% acrylamide gel (Laemmli, Nature (London) 227: 680–685 (1970)) under non-reducing conditions. A band of molecular weight (MW) 37–40 kDa was excised, digested with trypsin in situ, and the peptides separated by HPLC. One peptide was subjected to sequential Edman degradation, yielding the sequence Gly-Leu-Glu-Pro-Asp-Ala-Leu-Gly-Gly-Asn-Ala-Pro-Lys (SEQ ID NO:3). Sequencing was performed by the Keck Microsequencing facility at Yale University.

PCR:

Degenerate primers in both orientations were synthesized based on the amino acid sequence, and used to amplify an ASP gene-specific product from DNA isolated from an A. caninum $L_3$ cDNA library constructed in lambda ZAP II™ (Stratagene). The degenerate primers were paired with opposing flanking vector primers (T3 or T7 promoter) in preliminary experiments. The sense strand degenerate primer ASP-5 (SEQ ID NO: 11; Table 1) and the T7 primer (SEQ ID NO: 16; Table 1) amplified a product of approximately 550 bp, and therefore these primers were used to amplify DNA for cloning. The reaction conditions for PCR were 10 mM Tris-HCl (pH 9.0), 50 mM KCl, 0.1% Triton X-100, 1.5 mM $MgCl_2$, 0.2 mM of each dNTP, 1 U Taq DNA polymerase (Promega), and 75 ng of phage DNA containing the $L_3$ cDNA library in a 20 µl reaction. Ten identical reactions containing only the DNA and primers in 10 µl were subjected to "hot start" PCR (Arnheim and Erlich, Annual Review of Biochemistry 61: 131–156 (1992)) by heating at 94° C. for 5 minutes, then lowered to 85° C. for 5 minutes, during which time the remaining reaction components were added. The reactions were subjected to 30 cycles of 1 minute denaturation at 94° C., 1 minute annealing at 45° C., and 2 minutes extension at 72° C. Following amplification, the products were pooled and digested with PstI and KpnI. The digested DNA was electrophoresed in a 3% low melting point NuSieve™ GTG agarose gel (FMC Bioproducts) containing 0.5 µg/mL ethidium bromide.

A band of approximately 550 bp was excised, transferred to a microfuge tube, and melted at 65° C. The melted agarose was frozen in a dry ice-ethanol bath, and immediately centrifuged at 16,000×g for 10 minutes. The aqueous phase was transferred to a new tube, ethanol precipitated, resuspended in 7 µL of $dH_2O$, and cloned into pBluescript™ by standard methods. Double-stranded plasmid DNA was sequenced by the dideoxy method (Hattori and Sakaid (1986); Sanger et al. (1977)), using the Sequenase™ 2.0 kit (USB) and sequential synthetic oligonucleotide primers.

Library screening:

The A. caninum $L_3$ cDNA library was propagated in XLI-BLUE cells (Stratagene, La Jolla, calif.), and plated according to standard methods (Sambrook et al., Molecular Cloning: A Laboratory Manual (Cold Spring Harbor, Cold Spring Harbor Laboratory Press, 1989)). Approximately $2 \times 10^5$ plaques were screened with an RNA probe made by transcription of the 550 bp PCR product, using T3 RNA polymerase (Boehringer Manheim), in the presence of $\alpha$-[$^{32}$p]-UTP. Hybridization conditions were as follows: 6X SSPE (1X SSPE=150 mM NaCl/10 mM $NaH_2PO_4$/1 mM EDTA), 10X Denhardt's solution (1X=0.02% bovine serum albumin, 0.02% polyvinyl-pyrrolidone, 0.02% Ficoll 400), 1.0% SDS, 200 µg/mL yeast tRNA, 50% formamide, and the radiolabelled probe (approximately $1.2 \times 10^6$ cpm/mL) at 42° C. for 18 hours. Filters were washed with 2X SSC/0.1% SDS at 60° C. for 45 minutes, 0.2X SSC/0.1% SDS at 60° C. for 30 minutes, and 0.1X SSC/0.1% SDS at 60° C. for 60 minutes. Filters were exposed to XAR-5 film (Kodak) with an intensifying screen for 7 hours at −70° C. Eight positive clones from the tertiary screen were picked, and the phagemids containing the cDNAs were converted to plasmids (Bluescript™) by in vivo excision (Short and Sorge 1992). Plasmid DNAs were isolated by standard procedures, and digested with EcoRI and XhoI to release the inserts.

Two of the 8 clones were of different sizes, of approximately 1000 and 1200 bp. The 5' and 3' ends were sequenced using T3 and T7 primers, respectively. Both clones had poly(A) tails 3', and identical 3' sequences. The 5' ends were different, but further sequencing indicated that the shorter clone was a truncated version of the longer clone, renamed pASP-1. Restriction mapping indicated internal EcoRI and NcoI restriction sites at nucleotide positions 284 and 888 of SEQ ID NO: 1, respectively, which were utilized for subcloning to facilitate sequencing. Both strands were sequenced completely.

5' RACE:

A modified 5'-RACE technique was used to isolate the 5' end and start codon of the ASP cDNA (Frohman et al., Proceedings of the National Academy of Sciences USA 85: 8998–9002 (1988); Jain and Gomer, Biotechniques 12: 58–59 (1992); Templeton et al., Biotechniques 15: 48–51 (1993)). Approximately 400 mg of frozen A. caninum $L_3$ were ground to a powder in a mortar chilled in liquid nitrogen, and total RNA isolated using the TRIzol reagent (BRL). First strand cDNA was synthesized using M-MLV reverse transcriptase (Superscript™ II, BRL) and one pmole of ASP gene-specific primer 1 (GSP 1; SEQ ID NO: 12; Table 1) according to the manufacturer's protocol. The cDNA was ethanol precipitated in the presence of 10 µg of yeast tRNA, and resuspended in 200 µl $dH_2O$. The cDNA was 3'-tailed with in a 50 µl reaction containing 33.5 µl cDNA, 1 mM dGTP, and 15 U of terminal deoxytransferase (TdT, BRL) for 1 hour at 37° C. Following tailing, the reaction was extracted once with phenol:chloroform:isoamyl alcohol (25: 24: 1), ethanol precipitated, and resuspended in 150 µl of $dH_2O$. Two µl were used as template for the first PCR reaction, containing 25 pmoles of GSP 2 antisense primer (SEQ ID NO: 13), located internally to the primer used for RT (Table 1), together with 25 pmoles of a 5' poly(G) anchor primer (SEQ ID NO: 15; Table 1). The 50 µl reaction was subjected to 40 cycles of one minute at 94°

C., one minute at 48° C., and 1 minute at 72° C. Following amplification, 1 μl of the reaction was used in a second PCR reaction, which was identical to the first, except that a third nested antisense primer, GSP 3 (SEQ ID NO: 14; Table 1) with a 5' EcoRI restriction site, was substituted for GSP 2, and the annealing temperature increased to 55° C. Four reactions were pooled, extracted with phenol and chloroform, precipitated, and digested with BamHI and EcoRI. The inserts were gel purified, cloned into pBluescript™, and sequenced as above.

TABLE 1

Primers used for PCR and 5' RACE.

| | |
|---|---|
| ASP 5 | 5'-GGTACTGCAGGARCCNGAYGCNYTNGG-3' |
| GSP 1 | 5'-CCGACTCCATTATAGATGG-3' |
| GSP 2 | 5'-CCACCAGCCGGAGAGC-3' |
| GSP 3 | 5'-CTTGAATTCCAGCGAACGCGC-3' |
| Anchor | 5'-GAATCGATGGATCCTGCAGC$_{(17)}$ |
| T7 promoter | 5'-AATACGACTCACTATAG-3' |

R = A or G; Y = C or T; N = A, C, T, or G. Restriction sites PstI (ASP 5), EcoRI (GSP 3), and BamHI (anchor) used for cloning are underlined.

Western Blotting:

Concentrated ES products were electrophoresed in 11% polyacrylamide gel and transferred to Immobilon™-P PVDF membranes (Millipore) by electroblotting at 20V for 16 to 18 hours at 4° C. The membranes were blocked with 5% non-fat dry milk (Carnation) in PBS (NFDM) for 6 to 8 hours at 4° C. Following blocking, the membrane was incubated with a 1:1000 dilution of rabbit antiVespula squamosa antigen 5 (Vesq Ag5) antibody (a gift of Donald Hoffman, Dept. of Pathology, East Carolina University) in NFDM for 16–18 hours at 4° C. After 3 washes in NFDM, the membrane was incubated with a 1:5000 dilution of HRP-conjugated goat anti-rabbit secondary antibody (Sigma) for one hour at 22° C. Bands were visualized using Enhanced Chemiluminescence (Amersham).

EXAMPLE 2

EXPRESSION OF ASP.

Expression of ASP-1:

A 1 kb EcoRI/XhoI fragment containing the 3' end and poly(A) tail of ASP-1 was cloned in-frame into the pET28(c) expression vector (Novagen) and used to transform competent BL21 E. coli cells. Log-phase cells were induced by the addition of one mM IPTG, and incubated for three hours. One milliliter aliquots were removed after 0, 1, 2, and 3 hours of induction, and examined by SDS-PAGE and Western blotting.

Purification of ASP:

Two liters of induced BL21 cells containing the recombinant pET28: ASP plasmid were centrifuged, and the supernatant discarded. The pellet was resuspended in 60 mL of 50 mM Tris, pH 8.0/2 mM EDTA/0.1% Triton X-100 containing 100 μg/mL lysozyme, and incubated at 30 C. for 30 minutes. The solution was sonicated using a Branson 450 Sonifier equipped with a microtip for four minutes (output setting 3, 30% duty cycle) until no longer viscous. The solution was centrifuged at 12,000×g for 15 minutes, and the supernatant discarded. The pellet containing the expressed ASP was resuspended in 60 mL 1% SDS/0.5% 2-mercaptoethanol (2-ME), boiled for 5 minutes, and incubated at 22 C. for 14–18 hours (overnight). The lysate was transferred to dialysis membrane (12,000–14,000 molecular weight cut-off) and dialyzed against two liters of 0.1% SDS in PBS for two days, with two changes of buffer.

The pET28 expression system is designed to attach a short leader containing 6 histidine residues on the amino terminus of the expressed protein. This allows purification of the recombinant protein using a $Ni^{++}$ chelating resin (HisBind, Novagen) to bind the His tag. Recombinant ASP was purified from the cell extract according to the manufacturers's instructions, except that 0.1% SDS was added to the column buffers. The protein was eluted from the column with 1.0 M imidazole, dialyzed as above, and examined by SDS-PAGE. Protein concentration was determined by the bicinchoninic acid (BCA) method (BCA Protein Assay Kit, Pierce).

EXAMPLE 3

DETERMINATION OF BIOLOGICAL FUNCTION OF ASP.

In Vitro Activation Experiments:

METHOD

In vitro activation experiments were conducted to investigate the biological function of ASP. The first group of experiments were to determine the kinetics of ASP release. Individual wells containing approximately 5000 activated $L_3$ were harvested after 30 minutes, 1, 3, 6, and 24 hours of incubation, and the ES removed and concentrated by lyophilization. Non-activated $L_3$ incubated for 24 hours in RPMI alone were used as a negative control. A second kinetic experiment, in which the ES products of a single population of $L_3$ was sampled over time, was conducted as follows. A well containing approximately 5300 $L_3$ was incubated under standard activation conditions (see above). After 1, 3, 6 and 24 hours of incubation, the $L_3$ were removed, pelleted, and the supernatant transferred to a new tube and concentrated by lyophilization. The $L_3$ were returned to a new well, fresh medium containing the stimuli was added, and the incubation resumed, except at 24 hours, which was the terminal time point. A negative control (no stimuli) and a positive control (entire 24 hour ES output) were harvested at 24 hours.

The second type of experiment was to determine the effect of feeding inhibitors on the release of ASP. Approximately 2000 $L_3$ were incubated with 0.5 mM 4,7-phenanthroline, a known feeding inhibitor, and activation stimuli for 24 hours. Following incubation, the ES products were harvested as above. The ES products from all experiments were examined by Western blotting as described above.

RESULTS

When A. caninum $L_3$ are stimulated to resume feeding in vitro, they release a major product with a Mr of approximately 40 kDa, referred to as the Ancylostoma Secreted Protein. As described above, microsequencing of a tryptic digest of this protein revealed a peptide with the sequence N-Gly-Leu-Glu-Pro-Asp-Ala-Leu-Gly-Gly-Asn-Ala-Pro-Lys (SEQ ID NO:3). A degenerate primer derived from this sequence, together with a primer complementary to flanking vector sequence, amplified a fragment of approximately 550 bp from phage λ DNA containing an A. caninum $L_3$ cDNAs. This product was used as a probe to isolate a 1.2 kb cDNA clone encoding ASP from the A. caninum $L_3$ cDNA library. The cDNA contained a 3' poly(A) tail, but lacked a 5' initiation codon. The 5' end containing the ATG (Met) start codon was isolated from $L_3$ cDNA by 5' RACE. Four 5' end clones were sequenced, and found to encode untranslated leaders of variable sequence and length, but identical coding sequences that overlapped with the cDNA clone. The nucleotide sequences of untranslated 5' leader sequences isolated using 5' RACE of *A. caninum* L₃ cDNA are depicted in SEQ ID NO:4, SEQ ID NO:5, SEQ ID NO:6, and SEQ ID NO:7. None of the leaders contained the conserved nematode SL 1 or SL 2 (Bektesh and Hirsh, *Nucleic Acids Research* 16: 5692 (1988); Nilsen, *Annual Review of Microbiology* 47: 413–440 (1993); Spieth et al., *Cell* 73: 521–532 (1993)), nor could the 5' end be amplified from cDNA using an SL 1 primer and an internal gene specific primer.

The full length cDNA encodes an open reading frame (ORF) of 424 amino acids (nucleotides 1–1272 of SEQ ID NO:1), with a predicted molecular weight of 45,735 and an isolelectric point of 7.13. The full length cDNA also has a 34 bp 3' untranslated region (nucleotides 1273–1306 of SEQ ID NO:1). The entire sequence of the isolated peptide is present in the ORF (amino acids 255 to 267 of SEQ ID NO:2), confirming that this cDNA encodes the ASP molecule. The amino terminal 18 amino acids are highly hydrophobic, and a potential eukaryotic signal sequence cleavage site is located between amino acids 18 and 19 (von Heijne, *Nucleic Acids Research* 14: 4683–4690 (1986)).

Sequence editing, alignments and comparisons were performed using the GCG computer program (Genetics Computer Group Wisconsin Package) on a VAX 7610 computer. The potential signal sequence cleavage sites was determined using the PSIGNAL program (PC/GENE Release 5.18, Intelligenetics, Mountain View, Calif.) on a personal computer.

Database comparison (SwissProt) revealed significant homology between 215 amino acids of the carboxyl terminal of the ASP deduced amino acid sequence and the antigen 5 molecule of *Hymenoptera* venoms, whereas the amino terminal 191 amino acids failed to show significant homology to any proteins in the database. This homology is apparent by comparing the ASP deduced amino acid sequence (amino acids 192 to 406 of SEQ ID NO:2) with the amino acid sequences of representative *Hymenoptera* species, Dola. *Dolichovespula arenaria* (SEQ ID NO:8); Vesv. *Vespula vulgaris* (SEQ ID NO:9); and Pola. *Polistes annulatis* (SEQ ID NO:10). Western blots using Vesq Ag5, a polyclonal antibody against the antigen 5 of the yellowjacket *Vespula squamosa*, recognized a 40 kDa protein in activated, but not non-activated, *A. caninum* L₃ ES products. Additionally, this antibody recognized a protein of Mr=38 kDa in lysates of *E. coli* that express an approximately 1 kb 3' fragment of the ASP CDNA (amino acids 96 to 424 in SEQ ID NO:2), but not in uninduced bacteria. The anti-Ag 5 antibody recognized bands of slightly higher molecular weight (Mr approximately 42 kDa) in soluble extracts of *A. caninum* adults and L₃, and *A. braziliense*, *Strongyloides stercoralis*, and *Haemonchus contortus* L₃.

The in vitro kinetics experiments described above indicate that ASP is released within the first 30 minutes of incubation, and is released continuously thereafter, following larval activation. Inhibition of activation with the feeding inhibitor 4,7-phenanthroline, performed as described above, prevents the release of ASP. This indicates that release of ASP is associated with the activation of hookworm larvae.

Modifications and variations of the present invention will be obvious to those skilled in the art from the foregoing detailed description. Such modifications and variations are intended to come within the scope of the appended claims.

---

We claim:

1. An isolated nucleic acid molecule comprising a nucleic acid segment encoding all or a fragment of the amino terminal 191 amino acids of SEQ ID NO:2, wherein the fragment includes at least five consecutive amino acids of the amino terminal 191 amino acids of SEQ ID NO:2.

2. The nucleic acid molecule of claim 1 wherein the nucleic acid molecule encodes the amino acid sequence of SEQ ID NO:2.

3. The nucleic acid molecule of claim 1 further comprising a vector.

4. The nucleic acid molecule of claim 3 wherein the vector is an expression vector for a host selected from the group consisting of bacteria, yeast, insect cells, and mammalian cells.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 1320 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Anacylostoma caninum
        ( D ) DEVELOPMENTAL STAGE: Larva ( i x ) FEATURE:
        ( A ) NAME/KEY: terminator
        ( B ) LOCATION: 1273..1275

( i x ) FEATURE:
        ( A ) NAME/KEY: sig_peptide
        ( B ) LOCATION: 1..54

( i x ) FEATURE:
        ( A ) NAME/KEY: mat_peptide
        ( B ) LOCATION: 55..1272

( i x ) FEATURE:
        ( A ) NAME/KEY: CDS (B) LOCATION: 1..1272

(ix) FEATURE:
    (A) NAME/KEY: 3'UTR
    (B) LOCATION: 1273..1306

(xi) SEQUENCE DESCRIPTION: SEQ ID NO:1:

| | | | | | |
|---|---|---|---|---|---|
| ATGTTTTCAC | CTGTAATCGT | CAGTGTGATT | TTCACAATCG | CCTTCTGCGA | TGCGTCTCCA | 60 |
| GCAAGAGACG | GCTTCGGCTG | TTCAAACAGT | GGGATAACTG | ACAAGGACCG | GCAAGCATTC | 120 |
| CTCGACTTCC | ACAACAATGC | TCGTCGACGG | GTTGCGAAAG | GCGTTGAGGA | TAGCAACTCC | 180 |
| GGCAAACTGA | ATCCAGCGAA | GAACATGTAC | AAGCTGTCAT | GGACTGTGC | AATGGAACAG | 240 |
| CAGCTTCAGG | ATGCCATTCA | GTCATGCCCA | AGCGCGTTCG | CTGGAATTCA | AGGTGTTGCG | 300 |
| CAGAATGTAA | TGAGCTGGTC | AAGCTCTGGT | GGATTCCCCG | ATCCATCGGT | AAAGATAGAA | 360 |
| CAAACGCTCT | CCGGCTGGTG | GAGTGGTGCT | AAAAAGAACG | GCGTCGGCCC | GGACAACAAA | 420 |
| TACAACGGTG | GCGGTCTCTT | CGCCTTCTCT | AACATGGTAT | ACTCCGAAAC | GACGAAACTT | 480 |
| GGCTGCGCCT | ACAAGGTTTG | CGGCACTAAA | CTGGCGGTTT | CGTGCATCTA | TAATGGAGTC | 540 |
| GGGTACATCA | CAAATCAACC | TATGTGGGAG | ACAGGTCAGG | CTTGCAAGAC | AGGAGCAGAC | 600 |
| TGCTCCACTT | ACAAGAACTC | AGGCTGCGAG | GATGGCCTTT | GCACGAAAGG | ACCAGACGTA | 660 |
| CCAGAAACAA | ACCAGCAGTG | CCCCTCAAAC | ACTGGAATGA | CTGATTCAGT | CAGAGATACT | 720 |
| TTCCTATCGG | TGCACAATGA | GTTCAGGTCG | AGTGTTGCCC | GAGGTCTGGA | ACCCGACGCT | 780 |
| CTGGGCGGAA | ATGCACCAAA | AGCAGCTAAA | ATGCTCAAGA | TGGTGTATGA | CTGTGAAGTA | 840 |
| GAAGCATCGG | CCATCAGACA | TGGAAATAAA | TGCGTCTATC | AACATTCCCA | TGGCGAAGAC | 900 |
| AGACCTGGAC | TAGGAGAAAA | CATCTACAAG | ACTAGTGTAC | TCAAATTCGA | TAAGAACAAA | 960 |
| GCAGCCAAGC | AGGCTTCACA | ACTCTGGTGG | AATGAGTTAA | AAGAGTTCGG | CGTCGGCCCA | 1020 |
| TCCAACGTCC | TTACCACTGC | TTTATGGAAT | AGACCCGGCA | TGCAGATTGG | TCACTACACC | 1080 |
| CAGATGGCAT | GGGACACCAC | CTACAAACTT | GGATGTGCAG | TTGTTTTCTG | CAATGATTTC | 1140 |
| ACATTCGGTG | TTTGTCAGTA | TGGGCCAGGA | GGCAATTACA | TGGGTCATGT | CATCTACACT | 1200 |
| ATGGGCCAGC | CGTGTTCTCA | GTGTTCGCCT | GGTGCTACTT | GCAGCGTGAC | CGAAGGCTTG | 1260 |
| TGCAGTGCTC | CTTAATCAGT | TCTTAACAAT | GAATATCTTA | CAGTTGAAAA | AAAAAAAAA | 1320 |

(2) INFORMATION FOR SEQ ID NO:2:

(i) SEQUENCE CHARACTERISTICS:
        (A) LENGTH: 424 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Ancylostoma caninum
        (D) DEVELOPMENTAL STAGE: Larva (xi) SEQUENCE DESCRIPTION: SEQ ID NO:2:

Met Phe Ser Pro Val Ile Val Ser Val Ile Phe Thr Ile Ala Phe Cys
1               5                   10                  15

Asp Ala Ser Pro Ala Arg Asp Gly Phe Gly Cys Ser Asn Ser Gly Ile
                20                  25                  30

Thr Asp Lys Asp Arg Gln Ala Phe Leu Asp Phe His Asn Asn Ala Arg

```
            35                           40                          45

Arg Arg Val Ala Lys Gly Val Glu Asp Ser Asn Ser Gly Lys Leu Asn
        50                      55                  60

Pro Ala Lys Asn Met Tyr Lys Leu Ser Trp Asp Cys Ala Met Glu Gln
    65                  70                  75                      80

Gln Leu Gln Asp Ala Ile Gln Ser Cys Pro Ser Ala Phe Ala Gly Ile
                        85                  90                  95

Gln Gly Val Ala Gln Asn Val Met Ser Trp Ser Ser Gly Gly Phe
                    100                 105                 110

Pro Asp Pro Ser Val Lys Ile Glu Gln Thr Leu Ser Gly Trp Trp Ser
                115                     120                 125

Gly Ala Lys Lys Asn Gly Val Gly Pro Asp Asn Lys Tyr Asn Gly Gly
            130                     135                 140

Gly Leu Phe Ala Phe Ser Asn Met Val Tyr Ser Glu Thr Thr Lys Leu
    145                     150                 155                 160

Gly Cys Ala Tyr Lys Val Cys Gly Thr Lys Leu Ala Val Ser Cys Ile
                    165                 170                 175

Tyr Asn Gly Val Gly Tyr Ile Thr Asn Gln Pro Met Trp Glu Thr Gly
                180                     185                 190

Gln Ala Cys Lys Thr Gly Ala Asp Cys Ser Thr Tyr Lys Asn Ser Gly
                195                     200                 205

Cys Glu Asp Gly Leu Cys Thr Lys Gly Pro Asp Val Pro Glu Thr Asn
    210                     215                 220

Gln Gln Cys Pro Ser Asn Thr Gly Met Thr Asp Ser Val Arg Asp Thr
    225                 230                 235                 240

Phe Leu Ser Val His Asn Glu Phe Arg Ser Ser Val Ala Arg Gly Leu
                    245                 250                 255

Glu Pro Asp Ala Leu Gly Gly Asn Ala Pro Lys Ala Ala Lys Met Leu
                260                 265                 270

Lys Met Val Tyr Asp Cys Glu Val Glu Ala Ser Ala Ile Arg His Gly
            275                 280                 285

Asn Lys Cys Val Tyr Gln His Ser His Gly Glu Asp Arg Pro Gly Leu
    290                 295                 300

Gly Glu Asn Ile Tyr Lys Thr Ser Val Leu Lys Phe Asp Lys Asn Lys
    305                 310                 315                 320

Ala Ala Lys Gln Ala Ser Gln Leu Trp Trp Asn Glu Leu Lys Glu Phe
                    325                 330                 335

Gly Val Gly Pro Ser Asn Val Leu Thr Thr Ala Leu Trp Asn Arg Pro
                340                 345                 350

Gly Met Gln Ile Gly His Tyr Thr Gln Met Ala Trp Asp Thr Thr Tyr
            355                 360                 365

Lys Leu Gly Cys Ala Val Val Phe Cys Asn Asp Phe Thr Phe Gly Val
        370                 375                 380

Cys Gln Tyr Gly Pro Gly Asn Tyr Met Gly His Val Ile Tyr Thr
    385                 390                 395                 400

Met Gly Gln Pro Cys Ser Gln Cys Ser Pro Gly Ala Thr Cys Ser Val
                    405                 410                 415

Thr Glu Gly Leu Cys Ser Ala Pro
                420
```

( 2 ) INFORMATION FOR SEQ ID NO:3:

( i ) SEQUENCE CHARACTERISTICS:
  ( A ) LENGTH: 13 amino acids
  ( B ) TYPE: amino acid (C) STRANDEDNESS:
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
(A) ORGANISM: Ancylostoma caninum
(D) DEVELOPMENTAL STAGE: Larva (xi) SEQUENCE DESCRIPTION: SEQ ID NO:3:

```
Gly Leu Glu Pro Asp Ala Leu Gly Gly Asn Ala Pro Lys
 1               5                  10
```

(2) INFORMATION FOR SEQ ID NO:4:

(i) SEQUENCE CHARACTERISTICS:
(A) LENGTH: 62 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Ancylostoma caninum
(D) DEVELOPMENTAL STAGE: Larva (xi) SEQUENCE DESCRIPTION: SEQ ID NO:4:

```
ACCGCGGCCC GCTTTCTTG TTGTGCCGCT CTGTTATTTT CACACGGTTA CATCTTATCA    60
TG                                                                 62
```

(2) INFORMATION FOR SEQ ID NO:5:

(i) SEQUENCE CHARACTERISTICS:
(A) LENGTH: 62 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Ancylostoma caninum
(D) DEVELOPMENTAL STAGE: Larva (xi) SEQUENCE DESCRIPTION: SEQ ID NO:5:

```
CTAACGCTCT CTCTATTGTA TCACGCCTCC CGCATTTCAA TTCCCGGTTA CATCTTATCA    60
TG                                                                 62
```

(2) INFORMATION FOR SEQ ID NO:6:

(i) SEQUENCE CHARACTERISTICS:
(A) LENGTH: 36 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (vi) ORIGINAL SOURCE:
 (A) ORGANISM: Ancylostoma caninum
 (D) DEVELOPMENTAL STAGE: Larva (xi) SEQUENCE DESCRIPTION: SEQ ID NO:6:

```
GGTCCGGCAT AATCCTTCAC TCGACATCTT ATCATG                    36
```

(2) INFORMATION FOR SEQ ID NO:7:

(i) SEQUENCE CHARACTERISTICS:
 (A) LENGTH: 44 base pairs
 (B) TYPE: nucleic acid
 (C) STRANDEDNESS: double
 (D) TOPOLOGY: linear (ii) MOLECULE TYPE: cDNA (iii) HYPOTHETICAL: NO (iv) ANTI-SENSE: NO (vi) ORIGINAL SOURCE:
 (A) ORGANISM: Ancylostoma caninum
 (D) DEVELOPMENTAL STAGE: Larva (xi) SEQUENCE DESCRIPTION: SEQ ID NO:7:

```
GGGCTATAGG GAGCTCTTCG CGTTTCTTTC GTCATCTTAT CATG           44
```

(2) INFORMATION FOR SEQ ID NO:8:

(i) SEQUENCE CHARACTERISTICS:
 (A) LENGTH: 203 amino acids
 (B) TYPE: amino acid
 (C) STRANDEDNESS:
 (D) TOPOLOGY: linear (ii) MOLECULE TYPE: protein (iii) HYPOTHETICAL: NO (iv) ANTI-SENSE: NO (vi) ORIGINAL SOURCE:
 (A) ORGANISM: Dolichovespula arenaria (xi) SEQUENCE DESCRIPTION: SEQ ID NO:8:

```
Asn Asn Tyr Cys Lys Ile Cys Pro Lys Gly Thr His Thr Leu Cys Lys
 1               5                  10                  15

Tyr Gly Thr Ser Met Lys Pro Asn Cys Gly Gly Lys Ile Val Lys Ser
                20                  25                  30

Tyr Gly Val Thr Asn Asp Glu Lys Asn Glu Ile Val Lys Arg His Asn
             35                  40                  45

Glu Phe Arg Gln Lys Val Ala Gln Gly Leu Glu Thr Arg Gly Asn Pro
         50                  55                  60

Gly Pro Gln Pro Pro Ala Lys Asn Met Asn Leu Leu Val Trp Asn Asp
 65                  70                  75                  80

Glu Leu Ala Lys Ile Ala Gln Thr Trp Ala Asn Gln Cys Asn Phe Gly
                 85                  90                  95

His Asp Gln Cys Arg Asn Thr Ala Lys Tyr Pro Val Gly Gln Asn Val
                100                 105                 110

Ala Ile Ala Ser Thr Thr Gly Asn Ser Tyr Gln Thr Met Ser Tyr Leu
             115                 120                 125
```

-continued

```
Ile  Lys  Met  Trp  Glu  Asp  Glu  Val  Lys  Asp  Tyr  Asn  Pro  His  Lys  Asp
     130                      135                     140

Leu  Met  His  Asn  Asn  Phe  Ser  Lys  Val  Gly  His  Tyr  Thr  Gln  Met  Val
145                           150                     155                     160

Trp  Gly  Lys  Thr  Lys  Glu  Ile  Gly  Cys  Gly  Ser  Val  Lys  Tyr  Ile  Glu
                    165                     170                     175

Asn  Lys  Trp  His  Thr  His  Tyr  Leu  Val  Cys  Asn  Tyr  Gly  Pro  Ala  Gly
               180                      185                          190

Asn  Tyr  Met  Asn  Gln  Pro  Val  Tyr  Glu  Arg  Lys
          195                      200
```

( 2 ) INFORMATION FOR SEQ ID NO:9:

( i ) SEQUENCE CHARACTERISTICS:
( A ) LENGTH: 204 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
( A ) ORGANISM: Vespula vulgaris ( x i ) SEQUENCE DESCRIPTION: SEQ ID NO:9:

```
Asn  Asn  Tyr  Cys  Lys  Ile  Lys  Cys  Leu  Lys  Gly  Gly  Val  His  Thr  Ala
1                   5                   10                          15

Cys  Lys  Tyr  Gly  Ser  Leu  Lys  Pro  Asn  Cys  Gly  Asn  Lys  Val  Val  Val
               20                   25                          30

Ser  Tyr  Gly  Leu  Thr  Lys  Gln  Glu  Lys  Gln  Asp  Ile  Leu  Lys  Glu  His
          35                   40                          45

Asn  Asp  Phe  Arg  Gln  Lys  Ile  Ala  Arg  Gly  Leu  Glu  Thr  Arg  Gly  Asn
     50                   55                        60

Pro  Gly  Pro  Gln  Pro  Pro  Ala  Lys  Asn  Met  Lys  Asn  Leu  Val  Trp  Asn
65                   70                        75                          80

Asp  Glu  Leu  Ala  Tyr  Val  Ala  Gln  Val  Trp  Ala  Asn  Gln  Cys  Gln  Tyr
               85                        90                          95

Gly  His  Asp  Thr  Cys  Arg  Asp  Val  Ala  Lys  Tyr  Gln  Val  Gly  Gln  Asn
               100                      105                     110

Val  Ala  Leu  Thr  Gly  Ser  Thr  Ala  Ala  Lys  Tyr  Asp  Asp  Pro  Val  Lys
               115                      120                     125

Leu  Val  Lys  Met  Trp  Glu  Asp  Glu  Val  Lys  Asp  Tyr  Asn  Pro  Lys  Lys
     130                      135                     140

Lys  Phe  Ser  Gly  Asn  Asp  Phe  Leu  Lys  Thr  Gly  His  Tyr  Thr  Gln  Met
145                           150                     155                     160

Val  Trp  Ala  Asn  Thr  Lys  Glu  Val  Gly  Cys  Gly  Ser  Ile  Lys  Tyr  Ile
                    165                     170                     175

Gln  Glu  Lys  Trp  His  Lys  His  Tyr  Leu  Val  Cys  Asn  Tyr  Gly  Pro  Ser
               180                      185                          190

Gly  Asn  Phe  Met  Asn  Glu  Glu  Leu  Tyr  Gln  Thr  Lys
          195                      200
```

( 2 ) INFORMATION FOR SEQ ID NO:10:

( i ) SEQUENCE CHARACTERISTICS:
( A ) LENGTH: 205 amino acids
( B ) TYPE: amino acid (C) STRANDEDNESS: single
(D) TOPOLOGY: linear (ii) MOLECULE TYPE: protein (iii) HYPOTHETICAL: NO (iv) ANTI-SENSE: NO (vi) ORIGINAL SOURCE:
(A) ORGANISM: Polistes annulatis (xi) SEQUENCE DESCRIPTION: SEQ ID NO:10:

| Val | Asp | Tyr | Cys | Lys | Ile | Lys | Cys | Pro | Ser | Gly | Ile | His | Thr | Val | Cys |
| 1 | | | | 5 | | | | | 10 | | | | | 15 | |
| Gln | Tyr | Gly | Glu | Ser | Thr | Lys | Pro | Ser | Lys | Asn | Cys | Ala | Gly | Lys | Val |
| | | | 20 | | | | | 25 | | | | | 30 | | |
| Ile | Lys | Ser | Val | Gly | Pro | Thr | Glu | Glu | Lys | Lys | Leu | Ile | Val | Ser | |
| | | 35 | | | | | 40 | | | | | 45 | | | |
| Glu | His | Asn | Arg | Phe | Arg | Gln | Lys | Val | Ala | Gln | Gly | Leu | Glu | Thr | Arg |
| | 50 | | | | | 55 | | | | | 60 | | | | |
| Gly | Asn | Pro | Gly | Pro | Gln | Pro | Ala | Ala | Ser | Asp | Met | Asn | Asp | Leu | Val |
| 65 | | | | | 70 | | | | | 75 | | | | | 80 |
| Trp | Asn | Asp | Glu | Leu | Ala | His | Ile | Ala | Gln | Val | Trp | Ala | Ser | Gln | Cys |
| | | | | 85 | | | | | 90 | | | | | 95 | |
| Gln | Phe | Leu | Val | His | Asp | Lys | Cys | Arg | Asn | Thr | Ala | Lys | Tyr | Pro | Val |
| | | | 100 | | | | | 105 | | | | | 110 | | |
| Gly | Gln | Asn | Ile | Ala | Tyr | Ala | Gly | Gly | Ser | Asn | Leu | Pro | Asp | Val | Val |
| | | 115 | | | | | 120 | | | | | 125 | | | |
| Ser | Leu | Ile | Lys | Leu | Trp | Glu | Asn | Glu | Val | Lys | Asp | Phe | Asn | Tyr | Asn |
| | 130 | | | | | 135 | | | | | 140 | | | | |
| Thr | Gly | Ile | Thr | Lys | Gln | Asn | Phe | Ala | Lys | Ile | Gly | His | Tyr | Thr | Gln |
| 145 | | | | | 150 | | | | | 155 | | | | | 160 |
| Met | Val | Trp | Gly | Lys | Thr | Lys | Glu | Ile | Gly | Cys | Gly | Ser | Leu | Lys | Tyr |
| | | | | 165 | | | | | 170 | | | | | 175 | |
| Met | Glu | Asn | Asn | Met | Gln | Asn | His | Tyr | Leu | Ile | Cys | Asn | Tyr | Gly | Pro |
| | | | 180 | | | | | 185 | | | | | 190 | | |
| Ala | Gly | Asn | Tyr | Leu | Gly | Gln | Leu | Pro | Tyr | Thr | Lys | Lys | | | |
| | | 195 | | | | | 200 | | | | | 205 | | | |

(2) INFORMATION FOR SEQ ID NO:11:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA primer"

(iii) HYPOTHETICAL: NO (iv) ANTI-SENSE: NO (xi) SEQUENCE DESCRIPTION: SEQ ID NO:11:

GGTACTGCAG GARCCNGA Y G CN Y TNGG 27

(2) INFORMATION FOR SEQ ID NO:12:

(i) SEQUENCE CHARACTERISTICS:
(A) LENGTH: 19 base pairs
(B) TYPE: nucleic acid
(C) STRANDEDNESS: single (D) TOPOLOGY: linear (ii) MOLECULE TYPE: other nucleic acid
    (A) DESCRIPTION: /desc = "DNA primer"

(iii) HYPOTHETICAL: NO (iv) ANTI-SENSE: NO (xi) SEQUENCE DESCRIPTION: SEQ ID NO:12:

CCGACTCCAT TATAGATGG 19

(2) INFORMATION FOR SEQ ID NO:13:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "DNA primer"

(iii) HYPOTHETICAL: NO (iv) ANTI-SENSE: NO (xi) SEQUENCE DESCRIPTION: SEQ ID NO:13:

CCACCAGCCG GAGAGC 16

(2) INFORMATION FOR SEQ ID NO:14:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "DNA primer"

(iii) HYPOTHETICAL: NO (iv) ANTI-SENSE: NO (xi) SEQUENCE DESCRIPTION: SEQ ID NO:14:

CTTGAATTCC AGCGAACGCG C 21

(2) INFORMATION FOR SEQ ID NO:15:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "DNA primer"

(iii) HYPOTHETICAL: NO (iv) ANTI-SENSE: NO (xi) SEQUENCE DESCRIPTION: SEQ ID NO:15:

GAATCGATGG ATCCTGCAGC CCCCCCCCC CCCCC 36

(2) INFORMATION FOR SEQ ID NO:16:

(i) SEQUENCE CHARACTERISTICS:
    (A) LENGTH: 17 base pairs
    (B) TYPE: nucleic acid
    (C) STRANDEDNESS: single ( D ) TOPOLOGY: linear ( i i ) MOLECULE TYPE: other nucleic acid
    ( A ) DESCRIPTION: /desc = "DNA primer"

( i i i ) HYPOTHETICAL: NO ( i v ) ANTI-SENSE: NO ( x i ) SEQUENCE DESCRIPTION: SEQ ID NO:16:

AATACGACTC ACTATAG    17